(12) United States Patent
Krause et al.

(10) Patent No.: US 6,711,432 B1
(45) Date of Patent: Mar. 23, 2004

(54) COMPUTER-AIDED ORTHOPEDIC SURGERY

(75) Inventors: Norman M. Krause, Pittsburgh, PA (US); Lee E. Weiss, Pittsburgh, PA (US); Kenji Shimada, Pittsburgh, PA (US); Takeo Kanade, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 321 days.

(21) Appl. No.: 09/694,665

(22) Filed: Oct. 23, 2000

(51) Int. Cl.[7] .............................. A61F 2/30; A61B 5/103
(52) U.S. Cl. ........................ 600/427; 600/426; 128/922; 606/60; 395/924
(58) Field of Search .................... 128/898, 920, 128/923, 924; 600/427, 424, 411, 416, 425, 426; 606/53, 60; 623/16, 18; 395/924; 382/128, 131

(56) References Cited

U.S. PATENT DOCUMENTS

| | | | |
|---|---|---|---|
| 5,251,127 A | | 10/1993 | Raab |
| 5,279,309 A | * | 1/1994 | Taylor et al. ............... 128/782 |
| 5,526,812 A | | 6/1996 | Dumoulin et al. |
| 5,740,802 A | | 4/1998 | Nafis et al. |
| 5,749,362 A | | 5/1998 | Funda et al. |
| 5,765,561 A | * | 6/1998 | Chen et al. ............... 128/653.1 |
| 5,769,092 A | | 6/1998 | Williamson, Jr. |
| 5,799,055 A | | 8/1998 | Peshkin et al. |
| 5,806,518 A | | 9/1998 | Mittelstadt |
| 5,824,085 A | | 10/1998 | Sahay et al. |
| 5,871,018 A | | 2/1999 | Delp et al. |
| 5,880,976 A | * | 3/1999 | DiGioia III et al. ........ 364/578 |
| 5,970,499 A | * | 10/1999 | Smith et al. ................ 707/104 |
| 5,995,738 A | | 11/1999 | DiGioia, III et al. |
| 6,100,862 A | * | 8/2000 | Sullivan ....................... 345/88 |

OTHER PUBLICATIONS

Navab et al., Dynamic Geometrical Calibration for 3–D Cerebral Angiography, SPIE vol. 2708, (date unknown) pp. 361–370.

Brack et al., Towards Accurate X–Ray Camera Calibration in Computer–Assisted Robotic Surgery, 1996 Computer Assisted Radiology, pp. 721–728.

Schreiner et al., Accuracy Assessment of a Clinical Biplane Fluoroscope for Three–Dimensional Measurements and Targeting, SPIE, 1997, pp. 160–166.

Casperson, et al., Characterization of Aberrations in Image–Intensified Fluoroscopy, Medical Physics, vol. 3, No. 2, Mar./Apr. 1976, pp. 103–107.

Chakraborty, Image Intensifier Distortion Correction, Medical Physics, vol. 14, No. 2, Mar./Apr. 1987, pp. 249–252.

Rudin, et al., Accurate Characterization of Image Intensifier Distortion, Medical Physics vol. 18, No. 6, Nov./Dec. 1991, pp. 1145–1151.

(List continued on next page.)

Primary Examiner—Philip H. Leung
(74) Attorney, Agent, or Firm—Kevin A. Oliver; Foley Hoag LLP

(57) ABSTRACT

Devices and methods for implementing computer-aided surgical procedures and more specifically devices and methods for implementing a computer-aided orthopedic surgery utilizing intra-operative feedback. A three-dimensional model of an area of a patient upon which a surgical procedure is to be performed is modeled using software techniques. The software model is used to generate a surgical plan, including placement of multifunctional markers, for performing the surgical procedure. After the markers are placed on the patient, an updated image of the patient is taken and used to calculate a final surgical plan for performing the remainder of the surgical procedure. The three-dimensional modeling, surgical planning, and surgery may all take place remote from each other. The various entities may communicate via an electronic communications network such as the Internet.

44 Claims, 9 Drawing Sheets-

OTHER PUBLICATIONS

Champleoboux, et al., Form Accurate Range Imaging Sensor Calibration to Accurate Model–Based 3–D Object Localization, IEEE 1992, pp. 83–89.

Champleboux, et al., Accurate Calibration of Cameras and Range Imaging Sensors: the NPBS Method, IEEE 1992, pp. 1552–1557.

Schueler, et al., Correction of Image Intensifier Distortion for Three–Dimensional X–ray Angiography, SPIE, col. 2432, 1995, pp. 272–279.

Boone et al., Analysis and Correction of Imperfections in the Image Intensifier—TV—Digitizer Imaging Chain, Medical Physics, vol. 18, No. 2, Mar./Apr. 1991, pp. 236–242.

DiGioia, III, et al., Acetabular Component Orientation Using Surgical Navigation Technologies, presented Fourth Annual North American Program on Computer Assisted Orthopaedic Surgery, Jun. 15–17, 2000.

DiGioia, et al., Mini Incision THR Assisted with Surgical Navigation, Technologies, presented Fourth Annual North American Program on Computer Assisted Orthopaedic Surgery, Jun. 15–17, 2000.

Nikou, et al., Hybrid Reality Visualization Devices, presented Fourth Annual North American Program on Computer Assisted Orthopaedic Surgery, Jun. 15–17, 2000.

Nikou, et al., Augmented Reality Imaging Technology for Orthopaedic Surgery, Operative Techniques in Orthopaedics, No. 10, No. 1 (Jan. 2000), pp. 82–86.

DiGioia III, et al., Computer Assisted Orthopaedic Surgery, Clinical Orthopaedics, vol. 354, Sep., 1998.

DiGioia III, et al., Image Guided Navigation System to Measure Intraoperatively Acetabular Implant Alignment, Clinical Orthopaedics, vol. 355, Oct., 1998.

Simon, et al., The Fundamentals of Virtual Fluoroscopy, presented Fourth Annual North American Program on Computer Assisted Orthopaedics Surgery, Jun. 15–17, 2000.

Picard, et al., Surgical Navigation: "No Pre–Operative Images Necessary", presented Fourth Annual North American Program on Computer Assisted Orthopaedic Surgery, Jun. 15–17, 2000.

Bauer, et al., Robotics for Orthopaedics, presented Fourth Annual North American Program on Computer Assisted Orthopaedic Surgery, Jun. 15–17, 2000.

Abovitz, Human–Interactive Medical Robotics, presented Fourth Annual North American Program on Computer Assisted Orthopaedic Surgery, Jun. 15–17, 2000.

Bauer, et al., Pitfalls in Robotic Surgery, presented Fourth Annual North American Program on Computer Assisted Orthopaedic Surgery, Jun. 15–17, 2000.

Simon, A Framework to Evaluate Acuracy in CAOS, presented Fourth Annual Fourth American Program on Computer Assisted Orthopaedic Surgery, Jun. 15–17, 2000.

DiGioia III, et al., Computer–Assisted Tools and Interventional Technologies, The Lancet 2000, vol. 354, Dec., 1999.

Picard, et al., A Classification Proposal for Computer–Assisted Knee Systems, presented Fourth Annual North American Program on Computer Assisted Orthopaedic Surgery, Jun. 15–17, 2000.

Picard, et al., Intraoperative Navigation for TKR: Location of a Rotational Center of the Knee and Hip, presented Fourth Annual North American Program on Computer Assisted Orthopaedic Surgery, Jun. 15–17, 2000.

Miehlke, et al., Computer Integrated Instrumentation in Knee Arthroplasty, A comparative Study of Conventionall and Computerized Technique, presented Fourth Annual North American Program on Computer Assisted Orthopaedic Surgery, Jun. 15–17, 2000.

Jenny, et al., Computer–Assisted Total Knee Prosthesis Implantation Without Pre–Operative Imaging, presented Fourth Annual North American Program on Computer Assisted Orthopaedic Surgery, Jun. 15–17, 2000.

Picard, et al., Kneenav—TKR: Concept and Clinical Application, presented Fourth Annual North American Program on Computer Assisted Orthopaedic Surgery, Jun. 15–17, 2000.

Kunz, et al., Advanced Intraoperative Registration of Mechanical Limb Axes for Total Knee Arthroplasty Surgery, presented Fourth Annual North American Program on Computer Assisted Orthopaedic Surgery, Jun. 15–17, 2000.

Kunz, et al., A Novel Concept for Soft Tissue Balancing and Joint Line Navigation Criteria for Total Knee Arthroplasty, presented Fourth Annual North American Program on Computer–Assisted Orthopaedic Surgery, Jun. 15–17, 2000.

Muller, et al., Computer Assisted Preoperative Planning System for Total Knee Replacement, presented Fourth Annual North American Program on Computer Assisted Orthopaedic Surgery, Jun. 15–17, 2000.

Ellis, et al., Planning and Guidance of Tibial Osteotomies: Clinical Results, presented Fourth Annual North American Program on Computer Assisted Orthopaedic Surgery, Jun. 15–17, 2000.

Sati, A Review: Robotics and Navigation Systems for Reconstructive Ligament Surgery, presented Fourth Annual North American Program on Computer Assisted Orthopaedic Surgery, Jun. 15–17, 2000.

Sati, et al., Considering Anatomic and Functional Factors in ACL Reconstruction: New Technology, presented Fourth Annual North American Program on Computer Assisted Orthopaedic Surgery, Jun. 15–17, 2000.

Staubli, et al., Surface Anatomy Based Realtime Navigation for ACL—Reconstruction, presented Fourth Annual North American Program on Computer Assisted Orthopaedic Surgery, Jun. 15–17, 2000.

Picard, et al., Computer–Assisted ALC Reconstruction System: Rational and Preliminary Results, presented Fourth Annual North American Program on Computer Assisted Orthopaedic Surgery, Jun. 15–17, 2000.

Luities, et al., Computer–Assisted Anatomical Placement of a Double–Bundle ACL Through 3D Fitting or a Statistically Generated Femoral Template into Individual Knee Geometry, presented Fourth Annual North American Program on Computer Assisted Orthopaedic Surgery, Jun. 15–17, 2000.

Tonet, et al., An Augmented Reality Navigation System for Computer Assisted Arthroscopic Surgery of the Knee, presented Fourth Annual North American Program on Computer Assisted Orthopaedic Surgery, Jun. 15–17, 2000.

Petermann, et al., The Caspar–System (Computer Assisted Surgery Planning and Robotics) in ACL Reconstruction Experiences, Preliminary Results and New Developments, presented Fourth Annual North American Program on Computer Assisted Orthopaedic Surgery, Jun. 15–17, 2000.

Burkart, et al., A Method to Determine Precision and Repeatability of Tunnel Placement for ACL Reconstruction: A Comparison of Robotic and Traditional Techniques, presented Fourth Annual North American Program on Computer Assisted Orthopaedic Surgery, Jun. 15–17, 2000.

DiGioia III, Surgical Navigation and Image Guided Reconstructive Hip Surgery, presented Fourth Annual North American Program on Computer Assisted Orthopaedic Surgery, Jun. 15–17, 2000.

Lahmer, et al., Is Computer–Assisted Positioning of the Cup Necessary in Total Hip Replacement, presented Fourth Annual North American Program on Computer Assisted Orthopaedic Surgery, Jun. 15–17, 2000.

DiGioia III, et al., Unreliability of Mechanical Acetabular Alignment Guides and Ways to Improve Alignment, presented Fourth Annual North American Program on Computer Assisted Orthopaedic Surgery, Jun. 15–17, 2000.

Leenders, et al., Reduction of Abduction Angle of Acetabular Cup Position Using Computer Assisted Surgery, presented Fourth Annual North American Program on Computer Assisted Orthopaedic Surgery, Jun. 15–17, 2000.

Jaramaz, et al., Role of Bone vs. ProstheticImpingement in ROM Following THR, presented Fourth Annual North American Program on Computer Assisted Orthopaedic Surgery, Jun. 15–17, 2000.

Jaramaz, et al., HipNav Femur—Development of a Complete THR Application, presented Fourth Annual North American Program on Computer Assisted Orthopaedic Surgery, Jun. 15–17, 2000.

Jaramaz, et al., Variation in Radiographically Measured Cup Orientation, presented Fourth Annual North American Program on Computer Assisted Orthopaedic Surgery, Jun. 15–17, 2000.

Sugano, et al., Optotrak Navigation for Birmingham Hip Resurfacing, presented Fourth Annual North American Program on Computer Assisted Orthopaedic Surgery, Jun. 15–17, 2000.

Wiesel, et al., Comparison of Hand–Broached Versus Robot–Assisted Total Hip Replacement, presented Fourth Annual North American Program on Computer Assisted Orthopaedic Surgery, Jun. 15–17, 2000.

Bauer, et al., Primary and Revision THR Using the Robodoc System, presented Fourth Annual North American Program on Computer Assisted Orthopaedic Surgery, Jun. 15–17, 2000.

Decking, et al., The Caspar system for Cementless THR: Surgical Technique and Early Results, presented Fourth Annual North American Program on Computer Assisted Orthopaedic Surgery, Jun. 15–17, 2000.

Hasselbach, A Failure Protocol of the First 100 Robodoc THR, presented Fourth Annual North American Program on Computer Assisted Orthopaedic Surgery, Jun. 15–17, 2000.

Kahler, The Evolution of Computer Assisted Orthopaedic Surgery in Fracture Management, presented Fourth Annual North American Program on Computer Assisted Orthopaedic Surgery, Jun. 15–17, 2000.

Kahler, et al., Computer Guided Percutaneous Iliosacral Screw Fixation of Posterior Pelvic Ring Disruption Compared to Conventional Tecnique, presented Fourth Annual North American Program on Computer Assisted Orthopaedic Surgery, Jun. 15–17, 2000.

Barrick, et al., TOSCO Technique of Orthopaedic Surgery Computer Assistance Iliosacral Screw Insertion, presented Fourth Annual North American Program on Computer Assisted Orthopaedic Surgery, Jun. 15–17, 2000.

Mallik, et al., Optimizing Registration Accuracy in Computer Assisted Percutaneous Pelvic Surgery, presented Fourth Annual North American Program on Computer Assisted Orthopaedic Surgery, Jun. 15–17, 2000.

Gruetzner et al., Virtual Fluoroscopy in Acute Treatment of Pelvic Ring Disruptions, presented Fourth Annual North American Program on computer Assisted Surgery, Jun. 15–17, 2000.

Stockle, et al., Minimal Fluoroscopy: Safe Zones for Pelvic Screw Fixations, presented Fourth Annual North American Program on Computer Assisted Orthopaedic Surgery, Jun. 15–17, 2000.

Krivonos, et al., Minimal Invasive Surgery of the Pelvis Using Ultrasound, presented Fourth Annual North American Program on Computer Assisted Orthopaedic Surgery, Jun. 15–17, 2000.

Tonetti, et al., Clinical Experience of Ultrasound Registration. Application to Percutaneous Iliosacral Screwing of the Pelvic Ring, presented Fourth Annual North American Program on Computer Assisted Orthopaedic Surgery, Jun. 15–17, 2000.

Milner, et al., Application of CT Image Guided Computer Assisted Surgical Technology in Placement of Distal Interlocking Screws, presented Fourth Annual North American Program on Computer Assisted Orthopaedic Surgery, Jun. 15–17, 2000.

Kahler, Virtual Fluoroscopy: A Tool for Decreasing Radiation Exposure During Femoral Intramedullary Nailing, presented Fourth Annual North American Program on Computer Assisted Orthopaedic Surgery, Jun. 15–17, 2000.

Sanchez, et al., A Computer Assisted Surgery System with Pre–Operative Navigation and Semi–Active Robotic Operation. Application to Traumatology and Orthopaedic Surgery, presented Fourth Annual North American Program on Computer Assisted Orthopaedic Surgery, Jun. 15–17, 2000.

Foley, et al., Virtual Fluoroscopy: Multiplanar X–Ray Guidance with Minimal Radiation Exposure, presented Fourth Annual North American Program on Computer Assisted Orthopaedic Surgery, Jun. 15–17, 2000.

Foley, et al., Virtual Fluoroscopy for Cervical Spine Surgery, presented Fourth Annual North American Program on Computer Assisted Orthopaedic Surgery, Jun. 15–17, 2000.

Merloz, et al., Computer–Assisted Surgical Navigation Using Fluoroscopy First Clinical Use in Spine Surgery, presented Fourth Annual North American Program on Computer Assisted Orthopaedic Surgery, Jun. 15–17, 2000.

Rampersaud, et al., Radiation Exposure to the Spine Surgeon During Fluroscopically–Assisted Pedicle Screw Insertion, presented Fourth Annual North American Program on Computer Assisted Orthopaedic Surgery, Jun. 15–17, 2000.

Vandevelde, et al., Computer Planning and Image Guided Placement of Pedicle Screws for Spinal Deformities, presented Fourth Annual North American Program on Computer Assisted Orthopaedic Surgery, Jun. 15–17, 2000.

Kothe, et al., Computer Navigation of Parapedicular Screw Fixation in the Thoracic Spine, presented Fourth Annual North American Program on Computer Assisted Orthopaedic Surgery, Jun. 15–17, 2000.

Tamura, et al., Registration Accuracy of Computer Aided Lumbar Spine Surgery, presented Fourth Annual North American Program on Computer Assisted Orthopaedic Surgery, Jun. 15–17, 2000.

Choi, et al., Computer Assisted Fluoroscopic Targeting Systemm with a Robotic Arm for Pedicle Screw Insertion, presented Fourth Annual North American Program on Computer Assisted Orthopaedic Surgery, Jun. 15–17, 2000.

Pichora, et al., Case Report: A new Computer–Assisted Technique for Distal Radius Osteotomy, presented Fourth Annual North American Program on Computer Assisted Orthopaedic Surgery, Jun. 15–17, 2000.

Vandevelde, et al., The Use of Computer Assisted Technology for Navigation In Tumor Surgery, presented Fourth Annual North American Program on Computer Assisted Orthopaedic Surgery, Jun. 15–17, 2000.

Pandya, et al., The Application of the Neuromate Robot Quantitative Comparison with Frameles Infrared and Frame–Based Surgical Localization Systems, presented Fourth Annual North American Program on Computer Assisted Orthopaedic Surgery, Jun. 15–17, 2000.

Hasselbach, Case Report: Computer Assisted THR in a Girdlestone Hip with Malunion of the Femur, presented Fourth Annual North American Program on Computer Assisted Orthopaedic Surgery, Jun. 15–17, 2000.

Nakamura, et al., Real Time Laser–Pointing Endoscope Using Galvano Scanner and 955FPS High Speed Camera, presented Fourth Annual North American Program on Computer Assisted Orthopaedic Surgery, Jun. 15–17, 2000.

DiGioia III, Minimally Invasive Joint Resurfacing: Merging Biologics with Computer Assisted Surgical Technologies, presented Fourth Annual North American Program on Computer Assisted Orthopaedic Surgery, Jun. 15–17, 2000.

Gabriel, MicroElectroMechanical Systems (MEMS), presented Fourth Annual North American Program on Computer Assisted Orthopaedic Surgery, Jun. 15–17, 2000.

Delp, et al., Computer Assisted Knee Replacement, Clinical Orthopaedics, vol. 354, Sep., 1998, pp. 49–56.

Debski, et al., The Application of Robotics Technology to Joint Biomechanics Research, presented Fourth Annual North American Program on Computer Assisted Orthopaedic Surgery, Jun. 15–17, 2000.

Bauer, et al., Rationale for the Development of a new Robotic System for Computer Assisted Orthopaedic Surgery, presented Fourth Annual North American Program on Computer Assisted Orthopaedic Surgery, Jun. 15–17, 2000.

Taylor, What does the Future Hold for the Next Generation of Medical Robotics, presented Fourth Annual North American Program on Computer Assisted Orthopaedic Surgery, Jun. 15–17, 2000.

Long, et al., 3D Model for Long Bone from Two X–Ray Images By Matching with 2D/3D–Database, presented Fourth Annual North American Program on Computer Assisted Orthopaedic Surgery, Jun. 15–17, 2000.

Staubli, et al., Gender Specific Morphometric Surface Data for Computer Assisted ACL–Navigation, presented Fourth Annual North American Program on Computer Assisted Orthopaedic Surgery, Jun. 15–17, 2000.

Fukuda, et al., High and Low Payload–Robotic Systems to Study Knee Joint Function, presented Fourth Annual North American Program on Computer Assisted Orthopaedic Surgery, Jun. 15–17, 2000.

Gerhardt, et al., Improved Quality Control in Total Hip Replacement by the Finite Element Method Based on Computer Assisted Preoperative Planning, presented Fourth Annual North American Program on Computer Assisted Orthopaedic Surgery, Jun. 15–17, 2000.

Messmer, et al., Interactive Preoperative Planning of Internal Fixation on a Virtual 3D Model, presented Fourth Annual North American Program on Computer Assisted Orthopaedic Surgery, Jun. 15–17, 2000.

Malvisi, et al., Milling Bone: Comparison of the Temperature Elevation and Clinical Performances During Cutting, presented Fourth Annual North American Program on Computer Assisted Orthopaedic Surgery, Jun. 15–17, 2000.

Firoozbakhsh, et al., Pelvis Image Guided Surgery Plantom Study, presented Fourth Annual North American Program on Computer Assisted Orthopaedic Surgery, Jun. 15–17, 2000.

Robertson, et al., The Sensitivity of Carpal Bone Indices to Rotation Determined Using Digitally Reconstructed Radiographs, presented Fourth Annual North American Program on Computer Assisted Orthopaedic Surgery, Jun. 15–17, 2000.

Murphy, Total Hip Arthroplasty with an Uncemented Femoral Component Using Intra Operative Machining, presented Fourth Annual North American Program on Computer Assisted Orthopaedic Surgery, Jun. 15–17, 2000.

Zdravkovic, et al., Computer–Assisted Preoperative Planning (CAPP) in Orthopaedic Surgery, Computer Methods and Programs in Biomedicine, COMMET 01093, Elsevier Science Publishers B.V. (Biomedical Division), 1990, pp. 141–146.

Paley, et al., Ilizarov Technology, Advances in Operative Orthopaedics, vol. 1, Mosby Year Book, Inc., 1993, pp. 243–287.

Coquillart, Extended Free–Form Deformation: A Sculpturing Tool for 3D Geometric Modeling, Computer Graphics, vol. 24, No. 4, 1990, pp. 187–196.

Sederberg et al., Free–Form Deformation of Solid Geometric Models, presented at SIGGRAPH '86 Proceedings, Dallas, Texas, vol. 20, No. 4, 1986, pp. 151–160.

Coquillart, Extended Free–Form Deformation: A Sculpturing Tools for 3D Geometric Modeling, INRIA, Recherche, No. 1250, Programme 6, France, Jun. 1990, pp. 1–18.

Barr, Global and Local Deformations of Solid Primitives, Computer Graphics, vol. 18, No. 3, Jun. 1984, pp. 21–31.

Oh, et al., Systematic Reconstruction of 3D Curvilinear Objects From Two–View Drawings, Computers & Graphics, vol. 23, 1999, pp. 343–352.

Shin et al., Fast 3D Solid Model Reconstruction From Orthographic Views, Computer–Aided Design, vol. 30, No. 1, 1998, pp. 63–76.

Lawrence, et al., User's Guide for CFSQP Version 2.3: A C Code for Solving (Large Scale) Constrained Nonlinear (Minimax) Optimization Problems, Generating Iterates Satisfying All Inequality Constraints, published by the Electrical Enginering Department and the Institute for Systems Research, University of Maryland, College Park, Maryland 29742, 1995, pp. 1–69.

Stytz, et al., Three–Dimensional Medical Imaging: Algorithms and Computer Systems, ACM Computing Surveys, vol. 23, No. 4, Dec. 1991, pp. 421–499.

Masuda et al., A Cell–Based Approach for Generating Solid Objects from Orthographic Projections, a Research Report Published by IBM Research, Tokyo Research Laboratory, IBM Japan, Ltd., Nov. 13, 1995, pp. 1–29.

Yan, et al., Efficient Algorithm for the Reconstruction of 3D Objects from Orthographic Projections, Computer–Aided Design, vol. 26, No. 9, Sep. 1994.

Lin, et al., Computer–Assisted Surgery Planning for Lower Extremity Deformity Correction by the Ilizarov Method, Journal of Image Guided Surgery, vol. 1, 1995, pp. 103–108.

Viceconti, et al., A Software Simulation of Tibial Fracture Reduction with External Fixator, Computer Methods and Programs in Biomedicine, vol. 40, 1993, pp. 89–94.

Delorme, S., et al., "Three–Dimensional Modelling and Rendering of the Human Skeletal Trunk From 2D Radiographic Images", 3–D Digital Imaging and Modelling, 1999, Proceedings. Second International Conference on Ottawa, Ont., Canada Oct. 4–8, 1999, Los Alamitos, CA, US, IEE Comput. Soc., US.

Boljevic, Z. et al., "Computer–Assisted Three–Dimensional Modelling for Definition and Correction of Deformities in Orthopaedic Surgery", Proceedings of the International Conference on Information Technology Interfaces, Jun. 15, 1993 p. 357–364, Salata 7, Zagreb, Croatia.

Hong, Lin, et al., "The Cross–Sectional Image Guided Ilizarov Frame Positioning for the Surgery Planning of Lower Extremity Deformity Correction", Proceedings— 19$^{th}$ International Conference IEEE/EMBS, Oct. 30, 1997; Nov. 2, 1997, p. 767–769, Chicago, IL, USA.

Myoung–Hee Kim, et al., "Telediagnosis System for Orthopedic Deformity Analysis Based on 3D Medical Imaging", Proceedings of SPIE, vol. 3976, Feb. 13–15, 2000, p. 324–333, Seoul, Korea.

Cherkashin, A.M., et al., "Interactive Ilizarov Database: An Electronic Patient Record for Orthopaedics", Proceedings, Towards and Electronic Patient Record '96, Twelfth International Symposium on the Creation of Electronic Health Record System and Global Conference on Patient Cards, San Diego, CA, USA, vol. 2, May 13–18, 1996, p. 293–295, Newton, MA, USA.

* cited by examiner

COMPUTER-AIDED ORTHOPEDIC SURGERY

FIELD OF THE INVENTION

The present invention generally relates to devices and methods for implementing computer-aided surgical procedures and more specifically relates to devices and methods for implementing a computer-aided orthopedic surgery utilizing intra-operative feedback.

BACKGROUND OF THE INVENTION

Poorly aligned or misaligned bones can occur for a variety of reasons including congenital deformity and/or accidental disfigurement. A bone can be characterized as having an actual (or anatomical) axis that runs through the cross-sectional center of the bone and a mechanical axis that extends between the joints at either end of the bone and defines the movement of the bone. In a generally straight bone with joints in line with the anatomical axis, e.g., the tibia with the knee and ankle joints, the anatomical and the mechanical axes should almost coincide. In a nonlinear bone, e.g., the femur with off-center hip joint, the mechanical axis and the anatomical axis do not coincide even when the bone is correctly aligned.

The essence of a bone deformity or disfigurement occurs when the anatomical axis is altered to a point that the mechanical (motion) axis is not in its desired position. In a straight bone such as the tibia, the amount of disfigurement can be calculated as the deviation between the anatomical axis and the mechanical axis (because the axes should align in a straight bone). This deviation can cause discomfort, joint disease, decreased range of motion, and/or numerous other medical problems. To correct or limit these improper alignments, an orthopedic surgeon may perform corrective surgery on the deformed or disfigured bone to return symmetry between the axes.

One type of corrective orthopedic surgery is an osteotomy. Osteotomies are characterized by cutting one or more slices into a deformed bone to a depth sufficient to allow the bone to be "repositioned" in a way that aligns the actual axis of motion with the desired axis. Typically, the bone repositioning forms a "wedge" or gap of open space in the bone. This space is filled via bone graft to promote new bone growth, and some type of fixation mechanism is attached to the bone to keep the bone in its new (desired) orientation during the healing process.

The movement necessary to realign a disfigured or deformed bone often requires solving complex planning calculations as well as using a certain amount of estimation based upon the experience of the orthopedic surgeon. To aid in the accuracy of this process, several types of Computer-Aided Orthopedic Surgery (CAOS) are currently being developed. In general, CAOS involves a three step process: (1) generating a three-dimensional (3D) computerized model of the patient's bone; (2) performing a computer-aided pre-surgical analysis to generate a surgical plan that instructs a surgeon how to cut, fill, and/or reposition the bone as well as how to manipulate a robot during surgery; and (3) performing computer-aided surgery based on the pre-surgical plan.

The current methods of modeling an incorrectly aligned bone often include the use of Magnetic Resonance Imaging (MRI) or Computerized Axial Tomography (CAT) data. These imaging technologies are very expensive and may take an extensive amount of time for which to model a bone. Conventional CAOS methods often include robot-guided surgery or real-time tracking systems using highly technical equipment reserved for a few select surgeons in a very few locations. Therefore, a need has been recognized to provide the accuracy benefits of CAOS in a more cost effective, easy to use, and more widely available process than a conventional CAOS procedure. This improved CAOS process if preferably available to a wider body of patients and surgeons spread across a greater geographic and economic spectrum than current methods.

SUMMARY OF THE INVENTION

The present invention contemplates, in at least one preferred embodiment, devices and methods for computer-aided orthopedic surgery. More specifically, the present invention contemplates devices and methods for performing computer-aided surgical procedures, such as an open wedge osteotomy, using intra-operative feedback to improve the surgical outcome for the patient.

In at least one preferred embodiment of the present invention, a computer database includes one or more template bone models. Multiple X-rays of an incorrectly aligned bone are preferably taken and used to "morph" or modify a stored template bone model to create a 3D model of the misaligned bone. A computer program, running on a planning computer, may be used to aid in the generation of a pre-surgical plan for performing an osteotomy or other orthopedic surgery to correct bone alignment. The pre-surgical plan calculations may include: the positioning of multifunctional markers on the patient's bone and the parameters for manipulating one or more surgical tools such as an adjustable cutting guide, an adjustable fixation guide, or a combined cutting-fixation guide.

During surgery, a surgeon preferably affixes multifunctional markers to the misaligned bone according to the pre-surgical plan. A new set of fluoroscopic or X-ray images may be taken and used by the planning computer to update the pre-surgical plan into a final surgical plan based on the actual marker positions as depicted in the fluoroscopy. In this way, the updated fluoroscopic or X-ray images act as an intra-operative feedback system.

The surgeon preferably follows the updated surgical plan to cut the bone guided by an adjustable cutting guide and reposition the bone using an adjustable fixation guide (or these guides could be combined) Additionally, for example, in an open wedge osteotomy, the gap between cut sections of the bone are filled by bone graft and a fixation plate is attached thereto to hold the bone in its new orientation.

In at least one preferred embodiment, the planning computer exists at or near the same location as the surgical operating room. In other embodiments, the planning computer, template bone model database, operating room, and any other possible computers or devices may be located remotely from each other. These devices are preferably connected electronically, e.g., by way of the Internet. Such a distributed network allows access to the computer-aided osteotomy resources by an increased number of patients and surgeons than conventional methods. For example, this distributed system may be used to remotely access other experts, such as experienced orthopedic surgeons, during the planning or surgical stages.

These and other details, objects, and advantages of the present invention will be more readily apparent from the following description of the presently preferred embodiments.

BRIEF DESCRIPTION OF THE DRAWINGS

The invention and its presently preferred embodiments will be better understood by reference to the detailed disclosure hereinafter and/or to the accompanying drawings, wherein.

DETAILED DESCRIPTION OF THE PREFERRED EMBODIMENTS

The present invention broadly contemplates, in at least one preferred embodiment, a device and method for performing computer-aided surgery. The present invention may be specifically suited for performing computer-aided orthopedic surgery, such as an osteotomy, on a misaligned bone. The following description provides an example of using the present invention to perform an open wedge osteotomy, but the invention can be used for many types of orthopedic and other surgeries. Any reference to an open wedge osteotomy in particular is only by way of example.

Figure 1:
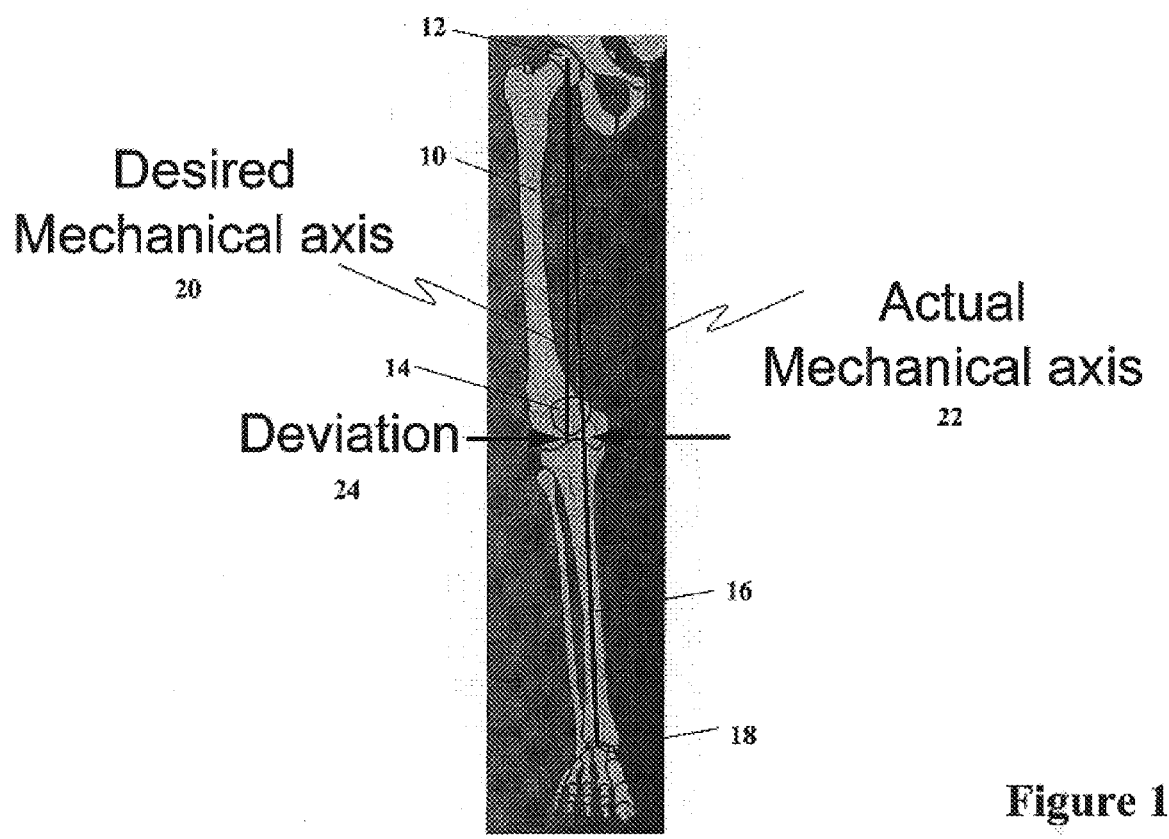
FIG. 1 shows a typical poorly aligned bone with reference axes.

FIG. 1 schematically shows an improperly aligned femur 10 and the resulting incorrect leg alignment. The FIG. 1 actual mechanical axis 22 represents the axis of motion from the hip joint 12 to the middle of the tibia 18 (near the ankle). If correctly aligned, this axis 12 should pass very close to the midpoint of the patella or kneecap 14 (shown as the desired mechanical axis 20). In the FIG. 1 example, there is a ideviation 24 between the desired 20 and actual 22 axes of motion. This deviation 24 represents the amount of femur 10 misalignment and can cause discomfort with decreased range of motion as well as other problems.

To correct these deformities, an orthopedic surgeon may perform an osteotomy or other surgery on the disfigured bone to return symmetry between these axes. Osteotomies are characterized by both the type of cut that is made in the bone (e.g., open wedge, closed wedge, center wedge) and the number of osteotomy sites (e.g., single, double). One type of osteotomy, an open wedge osteotomy, involves making a cut or wedge in the misaligned bone generally perpendicular to the long axis of the bone. Thereafter, depending on the desired bone realignment, the bone may be bent, twisted, and/or rotated about the cut sections until the "new" anatomical axis is properly aligned with the desired mechanical axis. Some type of fixation device, such as an internal plating system, may be used to hold the bone in its new orientation during the healing process after proper alignment is achieved, and a bone graft is used to fill in the open wedge to promote new bone growth.

As briefly described above, the movement necessary to realign a disfigured bone may be quite complex (movement around many different axes) and may require the solution of complex planning calculations as well as a certain amount of estimation based upon the experience of the orthopedic surgeon. To aid in the accuracy of this process, several types of Computer-Aided Orthopedic Surgery 50 (CAOS) have recently been researched. In general, as seen in the flow chart of FIG. 2A, CAOS 50 involves a three step process: (1) generating a 3D computerized model of the patient's bone 52; (2) performing a computer-aided pre-surgical analysis to aid in the creation of a surgical plan 54; and (3) performing computer-aided surgery based on the pre-surgical plan 56.

Figure 2:
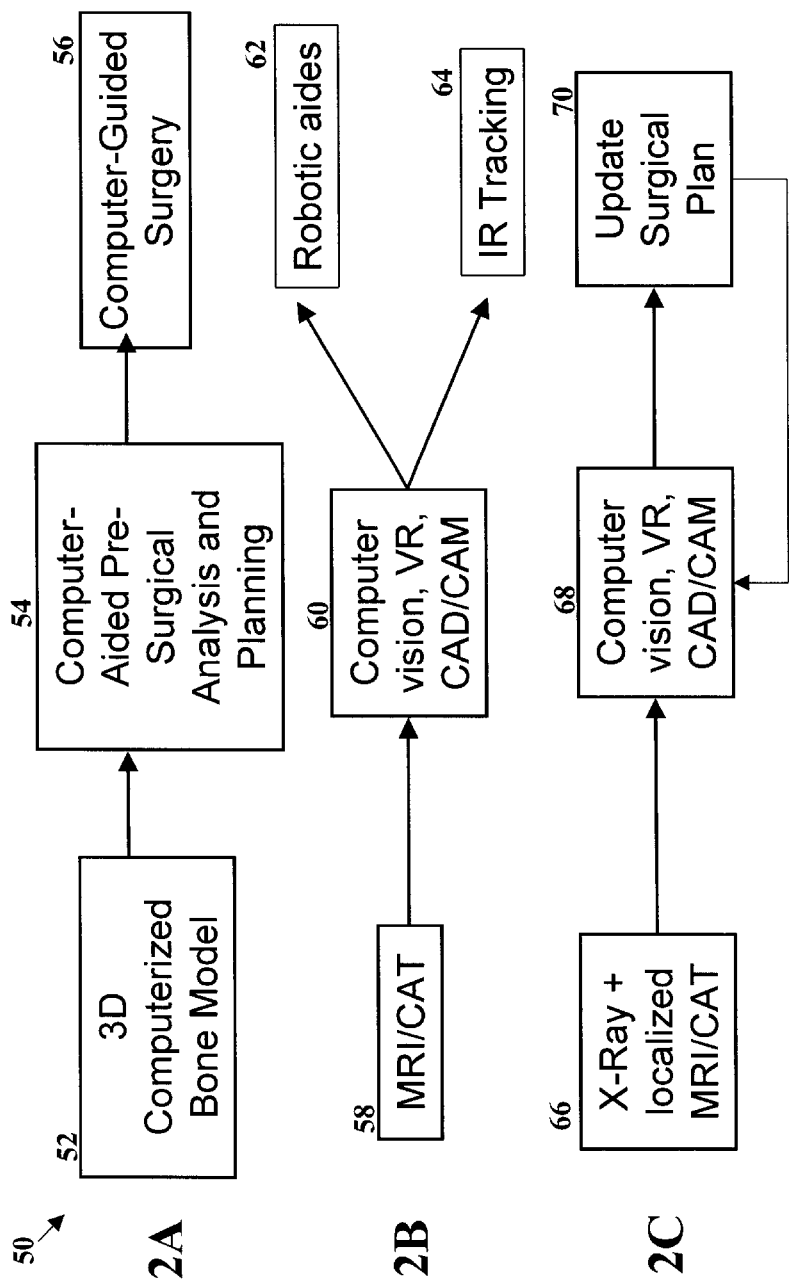
FIG. 2 is a block diagram of Computer-Aided Orthopedic Surgery (CAOS) methods including a general flow chart (2A), current methods (2B), and one embodiment of the present invention (2C)

Traditionally, as shown in FIG. 2B, the 3D computerized bone model is generated from MRI or CAT data 58 for the patient's bone. Use of the MRI or CAT data 58 may produce an accurate 3D computer model of the bone, but these techniques are expensive and typically require an extended amount of time to perform the MRI/CAT procedure and to model the bone. Also, although generally available, the equipment necessary to perform these procedures may not be found in smaller hospitals or remote areas. Therefore, the use of these 3D modeling techniques, even when accurate, may require a patient to go through the time and expense of traveling to a different hospital.

Once a 3D computerized bone model is generated, computer vision, Virtual Reality (VR), Computer Aided Design/Computer Aided Manufacture (CAD/CAM), numerical optimization, artificial intelligence (AI), and/or other techniques and technologies 60 may be used to help analyze the modeled bone and form a stepwise plan to carry out the surgery in the operating room. For example, a software program may compare the 3D model of the misaligned bone with existing models of properly aligned bones. The program may then determine, along a variety of different axes, an amount the bone needs to be moved in each direction. Alternatively, the program may just analyze the actual and desired positions of the joints (e.g., hip, knee, and ankle) to aid in the determination of where to cut the bone for the osteotomy and how to reposition the bone.

The result of any of these procedures will preferably be a set of instructions or guidelines for the orthopedic surgeon to follow during surgery. The surgical plan may also calculate the positioning of one or more surgical tools or bone markers to be used during the procedure. Alternatively, the surgeon may be provided with a range (e.g., within 2 mm. of a certain position) of acceptable choices. The surgical plan will also preferably guide the surgeon in relocating or repositioning the misaligned bone. This part of the plan will preferably detail for the surgeon various distances and rotation angles through which the bone should be moved.

The surgical plan may be sent to the surgeon using various media types including: still images and illustrations; static CAD models and/or interactive CAD models; computer animations; video or movie presentations; text descriptions including cutting locations and angles and settings for surgical tools; rapid prototype models, or some other media type. The surgeon preferably reviews the plan and determines whether or not the surgeon is comfortable with performing the surgery according to the plan. If the plan is not acceptable, the surgeon preferably provides feedback and suggestions about the plan to aid in the development of a new plan. This process may repeat until the pre-surgical plan is acceptable to the surgeon.

After the surgical plan is reviewed, a computer-aided surgery may be performed by a variety of methods. For example, in FIG. 2B the surgery may be performed using robotic aides 62 or some type of infrared (IR) tracking device 64. One type of robot-aided surgery employs robots with touch sensors that register a patient's actual bone geometry during surgery. This actual geometry is compared with the 3D pre-surgical bone model to give feedback to the robot or surgeon while performing the surgery. This feedback allows a robot or surgeon to follow the surgical plan more accurately than without the sensors.

Alternatively, an IR marker system could be used during surgery. For example, IR markers may be attached to the patient's bone and to the surgical tools at various locations. A real-time IR sensing system may track these markers and register them to the pre-surgical 3D model to provide feedback to the surgeon or to guide the surgeon to make precise surgical cuts according to the pre-surgical plan. Again, this feedback allows the surgeon to more accurately follow the surgical plan.

As with the full MRI or CAT data modeling 58, this real-time sensing and tracking of bone geometry using robotic aides 62 and/or IR sensing systems 64 is expensive, and only the most well-funded hospitals can afford the technology. Furthermore, many surgical procedures require computerized models of the entire limb (e.g., both the femur and the tibia of the leg) for generating the surgical plan, and acquiring MRI/CAT images of entire limbs may be both time-consuming and expensive.

Lower cost and more efficient and/or accessible surgical planning and performance methodologies are always desired. The present invention may improve upon conventional CAOS methods by replacing one or more of the above steps. For example, the MRI/CAT 3D-modeling step 58 and the computer-guided surgical procedures 62, 64 may be replaced with more cost effective and/or quicker approaches. The entire CAOS process 50 may be simplified and made more accessible for patients and surgeons by using less complex equipment and by locating certain computer equipment and planning resources in a centralized location.

The following example of the present invention describes using a planning computer and bone model database to generate a surgical plan for performing an orthopedic surgery. Much of the software involved, including the algorithms for generating a 3D model of the patient's bone were previously discussed in U.S. patent application Ser. No. 09/545,685 filed Apr. 7, 2000 entitled "Computer-Aided Bone Distraction" which is commonly owned with the present invention and is expressly incorporated by reference in its entirety herein. The following discussion will highlight the relevant portions of the previous application but will focus on previously undisclosed features.

In one aspect of the present invention, the 3D pre-surgical models of the misaligned bones may be created directly from readily available and inexpensive regular X-ray images 66. Initially, a 3D model of a "normal" or properly aligned reference bone may be generated. This "template bone model" or template bone model CAD data may be generated based on representative bone topographies from MRI or CAT data, or data from any other imaging technique. The template bone model may then be stored in a computer database for future access. The template bone model database preferably stores various different template bone models to be used for patients of different ages, genders, heights, and other characteristics. Alternatively or additionally, the bone models may be scalable or otherwise alterable to generate various-sized bone models. Once created and stored, each template bone model in this family of bone models can be used repeatedly and even shared among various surgeons, technicians, hospitals, or other interested users.

Figure 3:
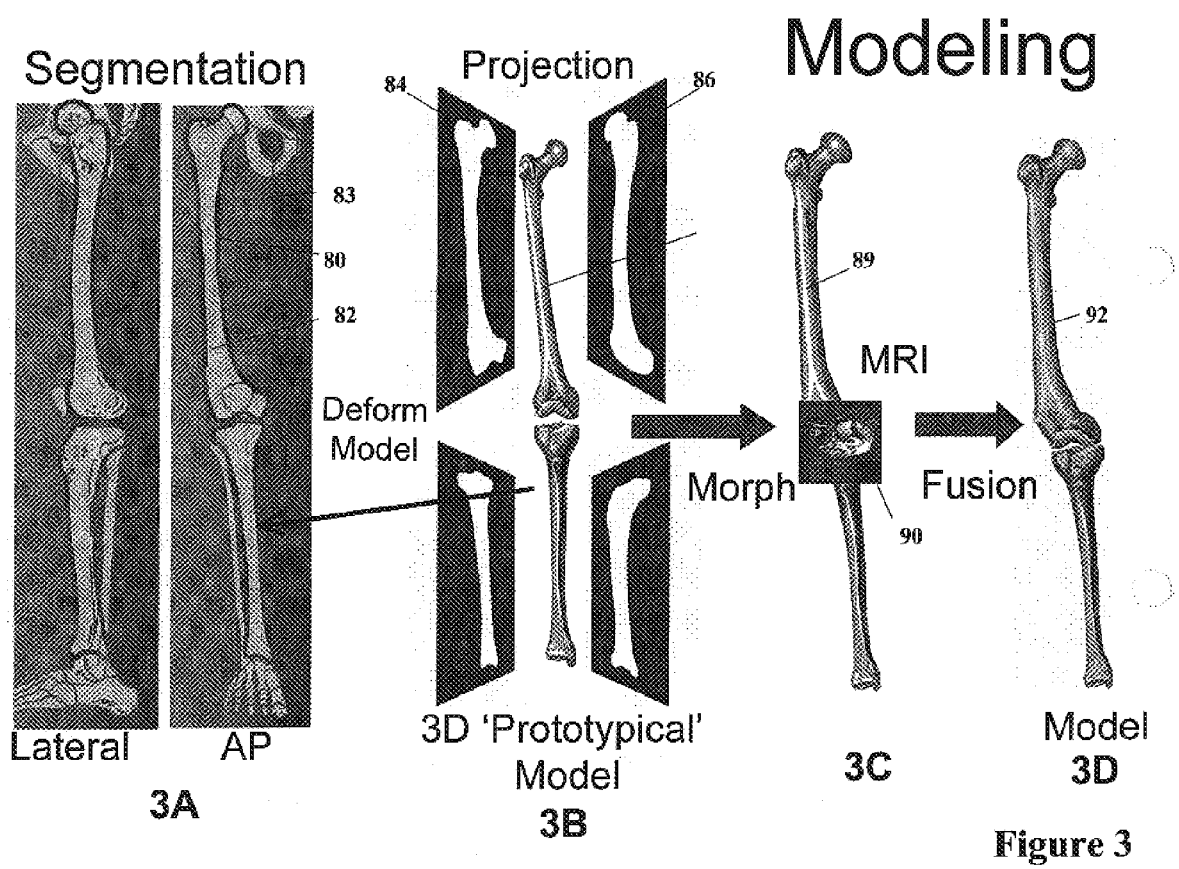
FIG. 3 details the bone modeling process including patient bone X-ray and segmentation (3A), template bone model (3B), localized MRI (3C), and the resulting fused image (3D)

Preferably, each of these 3D template bone models 88 can be graphically projected onto planes to produce a template bone model in a two-dimensional plane 84, 86 (see FIG. 3B). By projecting the 3D template bone model into at least two flat planes, preferably two planes that are orthogonal to each other, the template database or other computer can represent a bone as a series of two-dimensional pictures. An AP and lateral image projection of the template bone may be preferred. These two-dimensional projections may then be compared to X-rays or fluoroscopic images of a patient's bone to determine proper alignment. These template bones may exist in a computer database or other storage medium and can be shared, electronically or physically, with the users of several surgical planning computers.

The equipment used to generate the two- and three-dimensional template bone models is preferably a computer with advanced imaging and storage capabilities. The software algorithm is preferably able to convert the MRI, CAT, or other imaging data into a 3D "virtual" representation of the bone, as well as several flat projections of the bone. The template bone model preferably includes 3D positioning and scaling parameters as well as free-form deformation parameters as discussed in U.S. patent application Ser. No. 09/545, 685. These parameters allow the template bone model to be reshaped or "morphed" to resemble the patient's actual bone. This modeling computer may exist separate from the planning computer (see below) and/or any other device, or the modeling and planning computers may be integrated into one unit.

Once the template bone model has been created, the surgeon or technician may prepare a 3D software "model" of the patient's misaligned bone. Rather than generating the 3D model of the improperly aligned bone directly from MRI or CAT data as performed by conventional systems, the surgeon or other technician may alternatively use several regular X-ray images of the patient 66 (which are typically taken before any surgery). Preferably, at least a lateral and an AP (anterior-posterior) X-ray are taken of the patient's bone. The result of this imaging procedure is a series of two-dimensional representations of the patient's bone from various angles.

As shown in FIG. 3A, a software or other method may be used to segment 80 the patient's bone 82 in the X-ray images 83. Segmentation is characterized by determining the outer bounds 80 of the bones 82 in the X-rays 83. Segmentation may be accomplished using a light board and digitizing stylus. Because the AP, lateral and any other X-rays 83 are preferably taken orthogonal to each other, the resulting segmented bone represents a projection of the patient's bone on orthogonal planes similar to the two-dimensional orthogonal planes of the template bone models just described.

A software program or other method may analyze the X-rays of the patient's bone and compare it to the projections 84, 86 of the 3D template bone model 88 (FIG. 3B). If the template database contains more than one set of template bone models, the software may select the template bone model that most closely matches the patient's bone. The selection of a template bone model may occur based on patient history, or the selection may be based on comparing the patient X-rays 83 with two dimensional projections 84, 86 of the 3D template bone model 88. The software then determines how the template bone model should be altered to more accurately depict the patient's actual misaligned bone.

A "morphing" software program may be used to alter, bend, or morph the selected template bone model 88 in a way that causes the projections 84, 86 of the template bone model 88 to more closely match the two-dimensional segmented bone images 80 from the patient's X-rays 83. In effect, the 3D template bone model 88 is reshaped to resemble the patient's actual bone 82. The result of this process is a computer-modeled 3D representation of the patient's bone 89. The template bone model selection and morphing process may be performed on the modeling computer, the planning computer, a separate computer, or some combination of the three.

In a preferred embodiment of the present invention, the morphing software may alter the 3D template bone model 88 in small iterations until the projections of the 3D bone model 84, 86 match the X-ray or other images 83 of the patient's bone. For example, once an appropriate 3D template bone model 88 is chosen, the software may analyze the differences between the two-dimensional projections of the 3D template bone model 84, 86 and the segmented images 80 of the patient's bone. The software may then alter (stretch, bend, etc.) the 3D template bone model 88 in such a way that the template bone model projections will more accurately resemble the patient's X-ray images. The projections of the altered template bone model may then be compared to the X-ray images again. If the projections and the X-rays are not yet sufficiently similar, the software preferably alters the 3D bone model again to achieve similarity. The newly altered bone model may then be projected and compared to the patient's X-ray images another time. This process preferably continues until the 3D bone model has been altered sufficiently to make the projections match the patient's X-rays. When sufficient similarity occurs, the altered 3D bone model (3D patient bone model 89) should resemble the patient's actual bone.

This iterative reshaping may include a two-step process as described in U.S. patent application Ser. No. 09/545,685. For example, the positioning and scaling parameters may be optimized by rigid motion and scaling. An additional level of free-form deformation may be added for additional accuracy. As each iteration is completed, the 3D CAD data that defines the 3D patient bone model is preferably updated.

It should be noted here, that constructing a 3D patient bone model based on a pair of two dimensional X-rays will not typically result in a perfect representation of the patient's bone. The accuracy of the model is limited by geometric laws. In essence, the software algorithm described above codifies and improves upon the very method that a surgeon uses when looking at the same X-rays and then forming a mental picture of the patient's bone before surgery. The computer algorithm improves precision and makes this process easier for surgeons.

The "morphed" 3D patient bone model 89, which now portrays the patient's bone, can be used to provide gross information about the alignment of the bone's mechanical and anatomical axes. In some cases, this bone model information may not be of sufficiently high fidelity or quality to accurately model the more geometrically complex areas of the bone, e.g., the joints at the ends of the bones. This gross information may also not properly show the "twists" in the bone such as the relative orientation between the hip socket and the head of the femur. In these cases, more accurate, local models of the joints or other bone areas can be derived from fusing selective volumetric MRI/CAT scan data 90 for the joints with the morphed model 89 (see FIGS. 3C–3D). Portions of the 3D patient bone model may be reconstructed or refined using selected MRI cross-sectional slices of the patient's bone 90, or portions of the bone model may be completely replaced with the MRI data. FIG. 3C shows a "local" MRI 90 taken at the bottom of the femur to augment and clarify the morphed bone model 89 at an area of bone surface complexity. However, if the localized MRI information is not available, the morphed bone can still be used with the present CAOS invention as an improvement over current methods.

The result of this process is preferably a 3D software model 92 (based on 3D CAD data) of the patient's bone that is sufficient for computer-aided planning of the orthopedic surgery or other procedure. In contrast to conventional methods, this model 92 is preferably created using normal patient X-rays 83 and pre-existing template bone models 88 that may be generated once and then shared among various users at different imaging locations. This method may decrease the amount of time and money spent generating the 3D software model 92 of the patient's misaligned bone.

In addition to the 3D patient bone model 92 created on the computer, a rapid prototype model of the bone could be created using the stored 3D CAD data. The rapid prototype model is an actual, physical model of the bone made using conventional CAD/CAM or other modeling techniques. This rapid prototype model may be given to the surgeon to allow the surgeon to better visualize the misaligned patient bone before and even during surgery.

After the morphed 3D patient bone model 92 is generated, CAOS planner software developed as part of the present invention, may initially determine the osteotomy site location on the model. Alternatively, the surgeon may draw on his experience to choose a location for the osteotomy, and the location may be further optimized by the CAOS planning software. In some osteotomy procedures, the patient's bone may be so poorly aligned that a multiple osteotomy is needed to restore alignment to the bone. In these multiple osteotomies, the planning computer may be especially useful because of the complexities of the 3D model.

Figure 4:
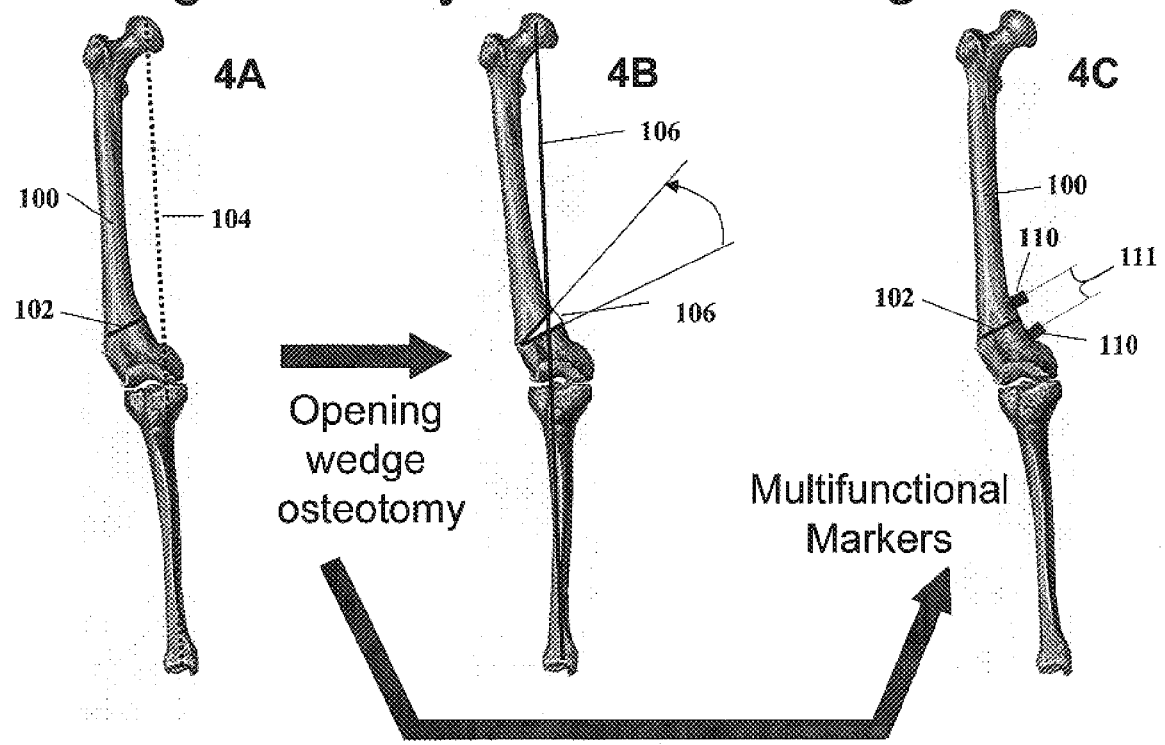
FIG. 4 details the pre-surgical planning process including the calculation of the bone cutting area (4A), bone wedge opening (4B), and placement of the multifunctional markers (4C)

The CAOS system preferably includes a planning computer that may or may not include the database of template bone models 88, the computer that modeled the original template bone models 88, or the computer that morphed the template bone model 88 to create the patient bone model 89. FIGS. 4A and 4B show a rudimentary determination of the proper osteotomy procedure. In FIG. 4A, the planning computer software analyzes the alignment of the leg bones 100 and the present mechanical axis of motion 104 (the dotted line from the ball joint in the hip to the bottom of the tibia in the ankle). FIG. 4A depicts the software's determination of a cutting location 102, and FIG. 4B depicts an opening "wedge" angle 106 as a possible solution that realigns the mechanical axis 107 through the middle of the patella.

Figure 5:
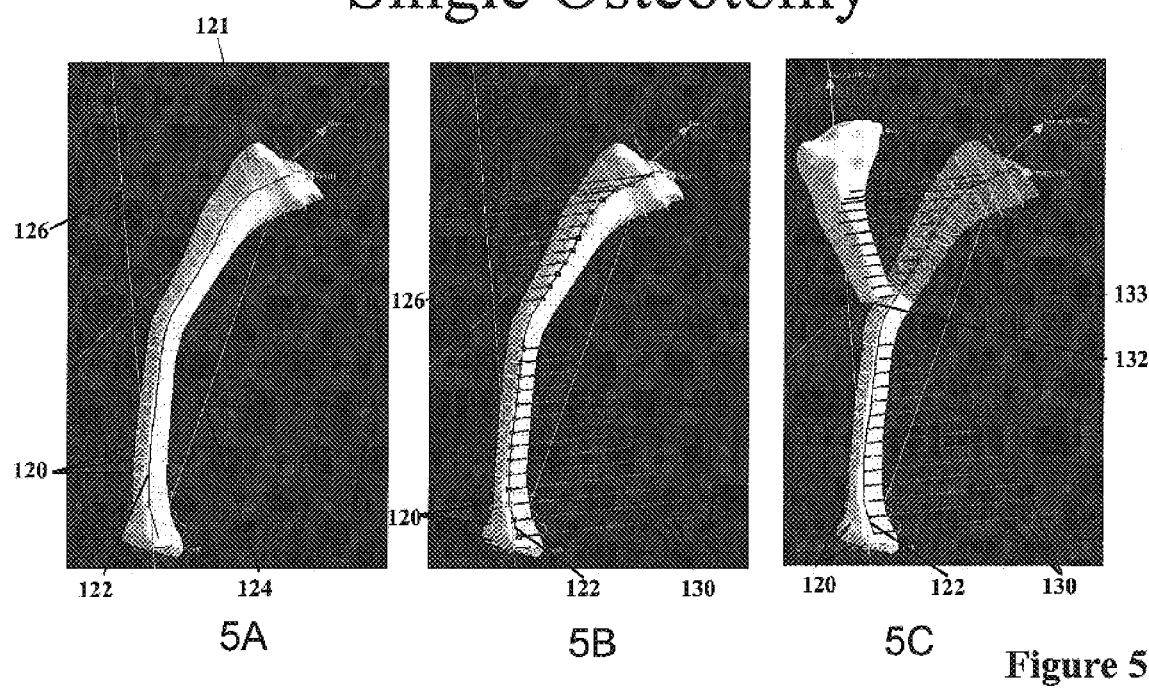
FIG. 5 details the offset analysis of a single osteotomy procedure.

There may be different software algorithms used for the various types of orthopedic surgeries. For a "simple" single osteotomy, the software algorithm may utilize the steps as set forth in FIG. 5. The single osteotomy entails locating an optimum place to cut the bone which limits the amount of bone movement needed to realign the bone during surgery.

FIG. 5A shows a 3D bone model 121 of a patient's misaligned bone. The planning software may initially determine an anatomical axis 122 through the center of the bone model 121. The computer may also calculated an existing mechanical axis 124 defined from the midpoint at one end of the bone down to the midpoint of the other end of the bone. The software algorithm preferably also calculates a desired mechanical axis 126 that will extend between the midpoints of the two ends of the bone after the osteotomy is performed. This desired mechanical axis 126 should begin at the existing midpoint of one end of the bone (shown extending from the lower end of the bone in FIG. 5A), and extend along the intended orientation of the bone.

The objective of the planning software is to determine at what location to cut the bone so that the relocation of the bone from its present mechanical axis 124 to the desired mechanical axis 126 is at a minimum. To accomplish this task, the anatomical axis 122 of the bone is preferably sliced or segmented at regular intervals 120 throughout the 3D model. These slices 120 are preferably taken perpendicular to the anatomical axis 122 of the bone 121. In the FIG. 5A example, there are 20 slices 120 taken.

The planning computer then preferably "virtually" cuts the bone model 121 at each of these 20 slice locations 120 and moves the upper section of the bone until the midpoint of the upper end of the bone is aligned with the desired mechanical axis 126 (FIGS. 5B–5C). The planning software may then compare the "new" midpoint (anatomical axis) of the bone section just above the bone slice 132 with the position of this same point before the relocation 133. The distance between these two points 132, 133 is the deviation that now exists between the upper and lower bone segments in FIG. 5C. The planning computer preferably calculates this deviation distance for each of the 20 (or any number) of slice 120 iterations and determines which osteotomy location has the smallest deviation (all deviations shown as 130). This location is preferably chosen as the preliminary site of the osteotomy.

A more complicated software methodology may be employed to perform the predictive analysis of the osteotomy. For example, a "rough" analysis to determine general location could then be followed up with a more refined analysis in the general vicinity of the predicted osteotomy location. Also, additional slices could be used for better resolution.

Figure 6:
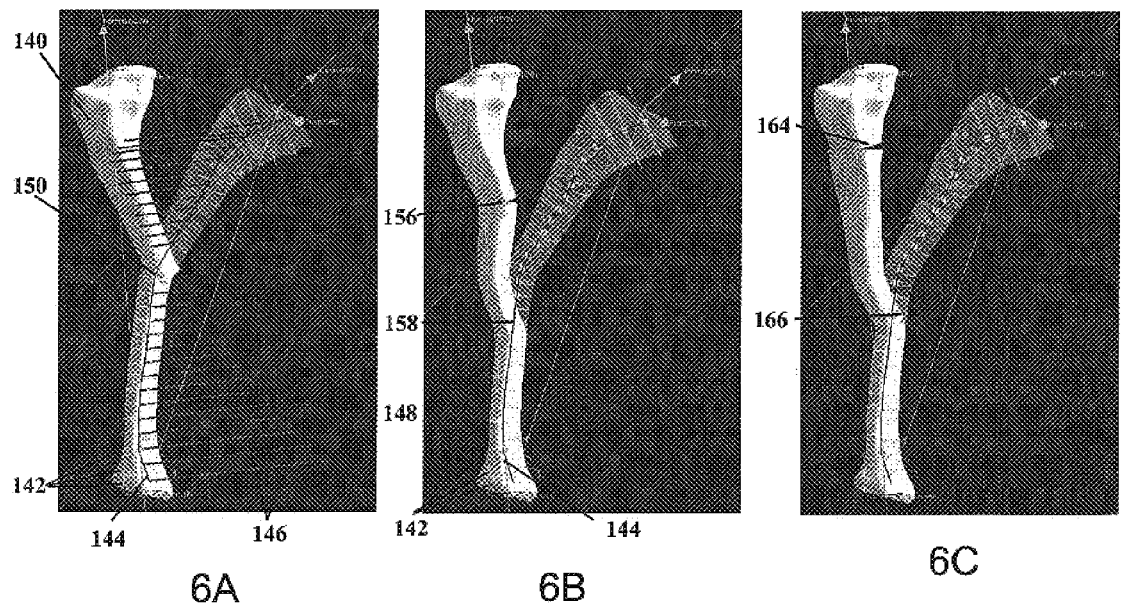
FIG. 6 details the offset analysis of a double osteotomy procedure.

FIG. 6 shows a possible software methodology for use with a double or multiple cut osteotomy planning procedure. The axes 144, 148, 150 and slice locations 142 in this method are preferably determine in the same way as the single osteotomy. However, the planning software may now perform a more complicated predictive analysis.

FIG. 6A shows that the same 20 virtual slices 142 are taken as in the single osteotomy procedure. However, the planning software preferably goes through all possible iterations of osteotomy locations. With a single osteotomy and 20 slices 142, there are 20 iterations. With a double osteotomy and 20 slices, there are just under 200 unique iterations (discounting the iterations that would duplicate the same osteotomy locations but in a different order).

For example, the planning software may start from the first slice location and "perform" a first virtual osteotomy (FIG. 6A). Thereafter, the planning software may calculate a second osteotomy performed from each of the other 19 slice locations. To calculate the effect of the osteotomy, the planning software preferably adds the deviation of the anatomical axes for both osteotomies together.

After these 19 (or any number) iterations have been modeled and the deviation results have been calculated, the planning computer preferably moves the first osteotomy location to the second slice and continues the analysis. The second osteotomy is preferably "made" at the other 19 slice locations, and the deviation results of the two cuts are preferably added to determine a total deviation.

After all 20 of the slice locations have been modeled with the other 19 slice locations for a second cut, the planning software preferably plots the results on a 3D diagram. For example, the X and Y axes could represent the first and second slice locations, and the Z axis could plot the total deviation at these two osteotomy locations. By examining the diagram, and looking for a Z axis minimum, the planning computer or surgeon may easily determine the appropriate locations for the double osteotomy or other multiple orthopedic procedures.

Although a surgeon may be able to visualize in his or her head the appropriate location for a single osteotomy, a double or higher order osteotomy, as shown in FIGS. 6B–6C, may be too complicated for such human analysis. In these cases, the CAOS method of the present invention may be especially useful.

After determining the proper procedure location, the computer-based planning software places multifunctional markers 110 near the suggested osteotomy location 102 on the computerized 3D patient bone model 100 (see, FIG. 4C). The multifunctional markers 110 may be used to both register bone location during surgery and anchor various surgical guides (e.g., a cutting guide to open the bone, a fixation guide to reposition the bone in the desired orientation during surgery, or a combined cutting-fixation guide). The optimizer or planning software may determine the appropriate location for the markers 110 based on mechanical tolerance data for the surgical guides that will be used during the surgery. Preferably, the guides and markers 110 have already been modeled by the planning computer. These multifunctional markers 110 may be detected during the surgery by X-ray, fluoroscopy, or other imaging methods to increase procedure accuracy over conventional surgical methods. The computer may provide an exact preferable location in which to place the markers 110, or the computer may offer a suggested range of marker positions (an allowable work envelope) within an acceptable tolerance limit.

Based on the computer-aided marker placement position, the planning computer preferably generates a "preliminary" surgical plan for the surgeon to follow in the operating room. This surgical plan may help the orthopedic surgeon decide whether or not to perform the surgery, and the plan may be used in the event the final surgical plan (explained below) is lost or electronically unavailable during surgery. This preliminary surgical plan preferably includes step-by-step guidelines for performing the orthopedic surgery. For example, the surgical plan may include various translation and rotation settings for an adjustable cutting guide used to locate and hold a reciprocating saw during surgery. Because the planning computer has previously calculated the location of the markers, and further because the adjustable cutting guide is anchored to the multifunctional markers during surgery, the cutting guide "settings" can be pre-calculated as part of the preliminary surgical plan. During the actual surgery, the surgeon need only set the cutting guide according to the plan and attach the guide to the markers (or attach the guide to the markers and then adjust the guide settings).

The planning computer may also calculate a pre-surgical plan for an adjustable fixation guide. This guide, which is preferably used to open the osteotomy wedge and reposition the incorrectly aligned bone, may also be anchored to the multifunctional markers. Because the marker position has previously been determined, the planning computer can also predetermine the fixation guide settings.

In an alternative embodiment, the cutting, fixation, or combined cutting-fixation guides may attach directly to the bone without the use of multifunctional markers. Preferably, these guides will be adapted for direct mounting to the bone using an adhesive, screw, or other device. Moreover, as described below, the present invention may be used when these guides are attached without the use of a pre-surgical plan, for example after a trauma. Images may be taken of the bone with attached guides, and a "final" surgical plan could be developed without the pre-surgical plan.

Once a planning computer has either modeled or simulated the osteotomy procedure, or has developed a detailed preliminary surgical plan, the simulation and/or plan is preferably sent to the surgeon to determine if the procedure will be performed. The surgical plan may be sent to the surgeon using various media types including: still images and illustrations; static CAD models and/or interactive CAD models; computer animations, video or movie presentations; text descriptions including cutting locations and angles and settings for surgical tools; rapid prototype models, or some other media type. The surgeon can preferably view the 3D computer simulation or other plan of the surgery and decide whether or not the plan is acceptable. If the surgeon does not "accept" the plan in its current embodiment, the surgeon may provide suggestions or comments that are sent back to the planning computer operator or to the surgical expert counseling the planning computer operator. The simulation and acceptance of the surgery may occur before a detailed preliminary surgical plan is developed, or the plan may be presented to the surgeon so they can proceed with the proposed plan or offer a new plan.

Once the patient's bone has been properly modeled and/or a preliminary surgical plan has been developed, the patient is ready to undergo the actual orthopedic surgical procedure. During surgery, radio-opaque multifunctional markers 110 are preferably attached to the patient's bone as both a location mechanism and as an anchor for the surgical guides (e.g., a cutting guide, fixation guide, combined cutting-fixation guide, and/or a calibration grid), These markers 110 may be small blocks that include a screw for mounting the markers to the bone and a screw acceptor (threaded hole) for attaching one or more guides thereto. Alternatively, the markers may be a threaded pin that is inserted into the patient's bone. Various surgical tools could be clamped to the end of the pin extending out of the bone during surgery.

At the beginning of the surgery, the surgeon is shown a CAD display or other representation of the pre-surgical plan depicting the required location/orientation of the osteotomy and the ideal location (and/or a tolerance zone) for the markers 110 to be placed on the patient's bone. The surgeon then exposes the patient's bone at the general location of the intended osteotomy and manually inserts the markers onto the bone (e.g., by screwing the markers into the bone) in approximate locations above and below the intended osteotomy. Because of the inherent inaccuracies associated with a surgeon trying to duplicate the location seen on a "picture" of the bone, the markers may or may not be placed in the exact desired location. Because of the accuracy of the plan, the surgeon may generally perform a minimally invasive surgery using a smaller incision than conventional methods.

In attaching the multifunctional markers to the patient's bone, it is preferable to align the axes that extend vertically through the top of the two markers (axes 111 in FIG. 4C) so that these axes are parallel to each other. If these axes are parallel, the markers 110 are "in the same plane" which will make mounting the various guides to the markers easier. This may also make the guides simpler to design as fewer degrees of freedom for placement are needed. To accomplish this alignment, a marker insertion guide (not shown) may be used to align the markers during positioning on the patient's bone.

The marker insertion guide is preferably a hollow metal tube with jagged edges towards one end. The jagged edges can "grab" the bone and secure the hollow tube while a drill bit is extended through the tube. The tube acts as a guide to make sure the markers are attached in the same plane. Various types of marker insertion guides are well-known in the medical arts.

Figure 7:
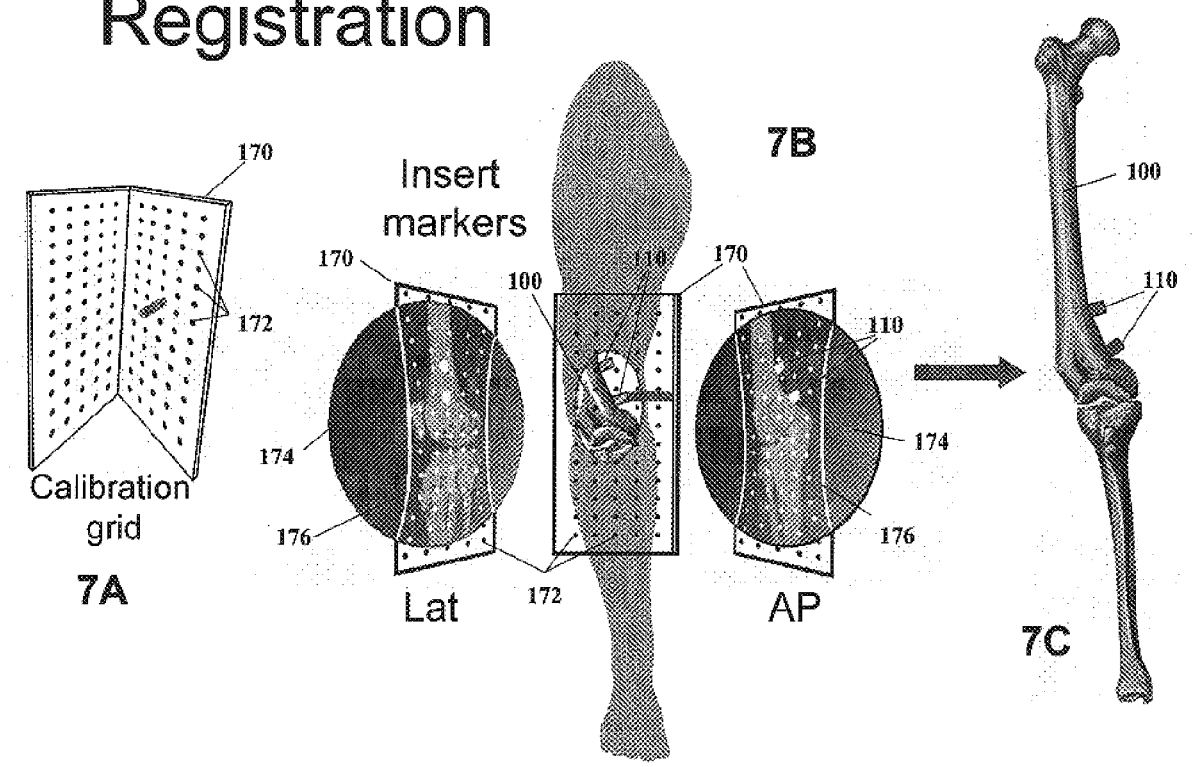
FIG. 7 details the multifunctional marker registration process including a calibration grid (7A), fluoroscopic image during surgery (7B), and resulting updated marker position bone model (7C)

After the markers 110 are attached, a translucent calibration grid 170 (with radio-opaque grid points or gridlines 172 printed thereon) may be mounted around the patient's bone (FIG. 7A). The calibration grid 172 preferably consists of two orthogonal grid sheets that are mounted around the outside of the surgical area such that they are parallel to the image plane of a lateral and AP fluoroscopic image of the misaligned bone. For example, the grid 170 may be mounted to the multifunctional markers 110. Upon imaging, the two-dimensional planar image 174 of the bone is set against the backdrop of the grid points 172. These grid points 172 are used to more accurately determine the positioning of the markers 110 and other areas of the bone by providing a background reference to aid in the "unwarping" of the fluoroscopic image.

After the calibration grid 170 is secured in place, one or more fluoroscopic images 174 are obtained for the exposed bone area including the attached calibration grid 170. Preferably, at least a lateral fluoroscopic image and an AP fluoroscopic image are obtained (FIG. 7B). A fluoroscopy is a low radiation imaging device that can be more flexible and useful in certain situations than obtaining X-ray images. A fluoroscopy machine is generally more maneuverable as compared to the bulkier and more cumbersome X-ray machine. However, fluoroscopy is often susceptible to image warping effects (see, e.g., 176) caused by surrounding magnetic or electromagnetic fields, sagging of the imaging source or other interference. The warping 176 of a fluoroscopic image of an object distorts the image. Therefore, image translation and further "unwarping" may be performed to remove or minimize resulting distortion 176. This type of fluoroscopic image correction is well-known in the art and is typically corrected using software techniques. The "warped" calibration grid points in the fluoroscopy can be used to unwarp the fluoroscopy image. When the imaged grid points are straight, the image has been unwarped correctly.

The corrected fluoroscopic image is generated on or sent to the planning computer, to determine the location of the markers 110 as precisely as possible in relationship to the 3D bone model. (FIG. 7D) The "new" or updated multifunctional marker position analysis may help negate the inherent problems with actual marker positioning (e.g., not being able to accurately place the markers according to the plan). The planning computer software preferably updates the locations of the earlier placed markers 110 on the 3D patient bone model 100 to reflect the actual marker locations on the patient's bone. With this updated information, the planning software may then re-calculate the pre-surgical plan settings for the cutting guide, fixation guide, combined cutting-fixation guide, and any other device used during the surgery.

In essence, the pre-surgical plan may be updated to correct the inherent errors in placing the markers by hand during surgery. Using this intra-operative feedback during the surgery, a more accurate surgical plan can be calculated by the planning computer.

After the new or "final" surgical plan is calculated, the surgeon is ready to actually perform the osteotomy. The osteotomy preferably begins by cutting the bone so that the bone can be repositioned according to the desired axis of motion. The bone is typically cut using a reciprocating or "gigley" hand-held saw that is less damaging to surrounding tissues and cells. To more accurately control the cut made by the reciprocating saw, an adjustable cutting guide 190, such as the one shown in FIG. 8A, may be used.

Figure 8:
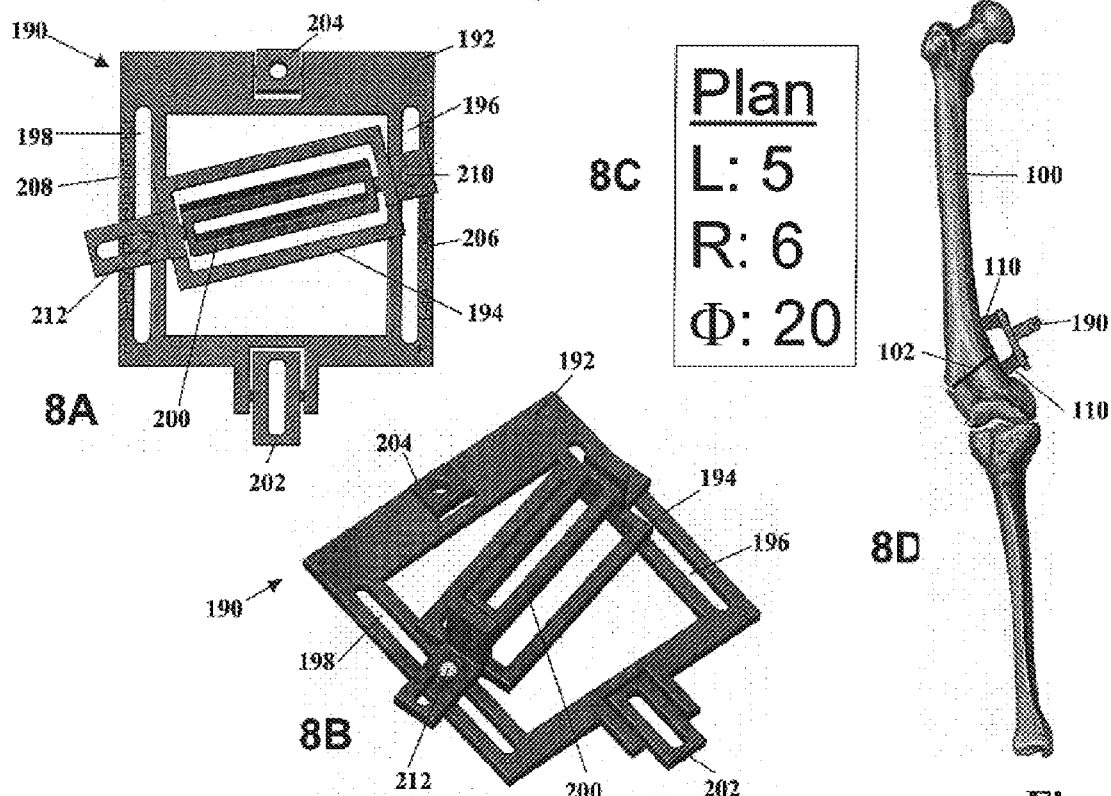
FIG. 8 details a top (8A) and isometric (8B) view of an adjustable cutting guide including exemplary surgical plan (8C) and a front view of the cutting guide mounted to the multifunctional markers (8D)

FIG. 8A details a top view and FIG. 8B shows an isometric view of a manually adjustable cutting guide 190 that may be mounted onto the multifunctional markers 110 secured to the patient's bone 100. The cutting guide 190 is comprised of a base plate 192 and a cutting guide member 194. The base plate 192 preferably has two anchor slots 202, 204 through which a screw or other attachment device may be inserted so that the adjustable cutting guide 190 can be secured to the multifunctional markers 110 on the patient's bone 100. The base plate 192 may also include two adjusting slots 196, 198 for setting the proper positioning of the cutting guide member 194. The two adjusting slots 196, 198 are preferably marked with indicators 206, 208, in this case numbers, that correspond to the surgical plan that the planning computer outputs for the surgeon.

The cutting guide member 190 includes two screws 210, 212 or other adjusting devices that are integrally located within the adjusting slots 196, 198. In the center of the cutting guide member 194, there is preferably a saw slot 200 that can be rotatably adjusted to accommodate a reciprocating saw at a variety of angles for cutting the patient's bone.

In practice, the adjustable cutting guide 190 may allow the surgeon to more accurately recreate a cut in the patient's bone as modeled by the planning computer. Preferably, the surgical plan calculated by the planning computer, after being updated to reflect the actual positioning of the radioopaque multifunctional markers 110 on the patient's bone, includes a preferred "setting" for the adjustable slots 196, 198, as well as a preferred angle $\Phi$ for the saw slot 200. One such example plan is shown in FIG. 8C.

The slot settings 206, 208 for the adjustable cutting guide 190 are preferably used to locate, along at least two axes, the reciprocating saw used to cut the patient's bone. For example, by altering the relative position of the slot settings with respect to each other, the cutting guide member 194 may be rotated in a plane perpendicular to the face of the patient's bone (looking down on the bone from above). If the right slot setting 206 is set to 5, and the left setting 208 is moved from 1 up through 12, the cutting guide member 194 will rotate in a clockwise direction. Because the left set screw 212 of the cutting guide member 194 preferably has a slotted opening rather than a simple hole (as on the right side 210), the cutting member 194 is preferably capable of being rotated. If both the left and right set screws 210, 212 of the cutting guide member were in circular holes, the cutting guide member 194 would only be able to slide back and forth in the base member adjustable slots 196, 198.

In addition to setting the vertical rotation of the cutting guide member 194, the slot settings 206, 208 also determine at what location relative to the multifunctional markers 110 the cut should be made. For example, if both slot settings 206, 208 are increased by the same amount, the cutting guide member 194 will slide up towards the top marker while maintaining the same rotational setting. Likewise, if the slot settings 206, 208 are decreased in equal amounts, the cutting guide member 194 will move towards the lower marker. Both slot settings 206, 208 are preferably manipulated and set via manual setting devices such as a set screw 210, 212 or small bolt used to tighten the cutting guide member 194 in the desired position. Because the surgical plan preferably displays the appropriate guide settings to the surgeon and the adjustable cutting guide slots are pre-marked, use of the cutting guide may be quicker, easier, and more accurate than conventional methods.

The surgical plan also preferably includes an angle $\Phi$ for which the saw slot 200 is to be rotated and secured within the center of the cutting guide member 194. As with the base plate slots 206, 208, the saw slot 200 is preferably pre-marked with angle demarcations (not shown) that allow for easy adjustment of the saw slot 200 to a desired cutting plane angle. The saw slot 200 may then be secured in a desired position by way of a set screw or some other temporary fixation device.

Once the three (or more) settings for the adjustable cutting guide 190 are set according to the updated surgical plan, the cutting guide 190 is preferably attached to the patient's bone 100 (or the guide 190 may be attached to the bone 100 before setting). Preferably, the base plate 142 of the adjustable cutting guide 190 includes two mounting slots 202, 204 through which a screw or other mounting device can be inserted to affix the adjustable cutting guide 190 to the multifunctional markers 110. The first mounting slot 204 is preferably a hole slightly larger than the mounting screw so that the cutting guide 190 is unable to slide with respect to the markers 110 during surgery. The second mounting slot 202 is preferably oval or slotted to accommodate a slight "misplacement" of the multifunctional markers 110 on the patient's bone 100. Because the markers 110 may not be placed at exactly the desired distance apart from each other, the mounting slots 202, 204 can preferably accommodate the markers 110 at slightly greater or smaller distances from each other. FIG. 8D shows the adjustable cutting guide 190 mounted to the multifunctional markers 110 on an exposed bone 100 with the skin and other tissues removed for clarity.

After the adjustable cutting guide 190 is mounted to the bone 100, the surgeon preferably inserts a reciprocating saw or other cutting device into the saw slot 200 of the cutting guide 190 and cuts the patient's bone 100 according to the surgical plan. The saw slot 200 may include a mechanical stop that prevents the saw from cutting a slot in the bone of more than the desired depth. After the osteotomy cut is made, the saw is removed from the cutting guide 190 and the cutting guide is dismounted from the bone 100 by unscrewing it from the multifunctional markers 110.

Figure 9:
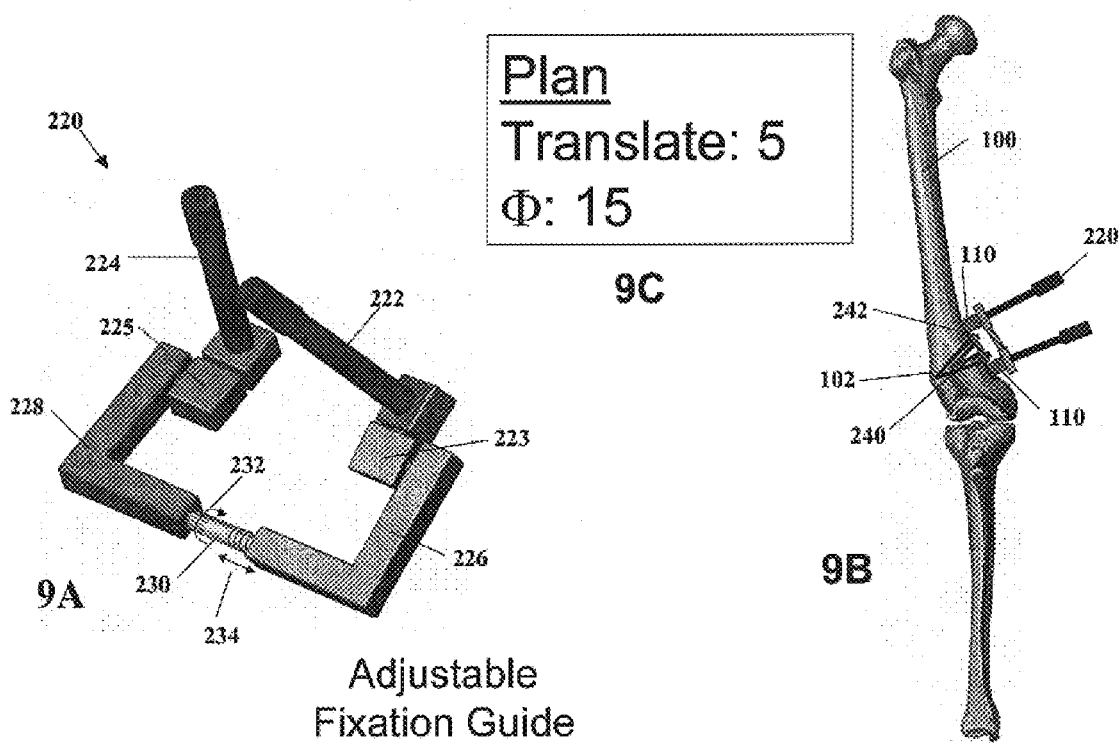
FIG. 9 details an isometric view (9A) of an adjustable fixation guide including surgical plan (9C) and a front view of the fixation guide mounted to the multifunctional markers with attached fixation plate (9B).

After the cutting guide 190 is removed from the bone 100, and with the multifunctional markers 110 still attached to the bone, the bone is ready to be bent, rotated, twisted, and/or repositioned into the proper alignment according to the updated surgical plan. The cut 102 in the bone 100 has been made, and the wedge may now be opened. FIG. 9A shows an exemplary adjustable fixation guide 220 for use in repositioning an improperly aligned bone. The purpose of the adjustable fixation guide 220 is preferably to force the bone 100 into the newly desired position with a greater amount of accuracy compared to conventional methods. Again, this part of the surgical plan has been "updated" based on the actual position of the multifunctional markers.

The adjustable fixation guide 220 pictured in FIG. 9A allows for movement of the bone along two axes: (1)

lengthening the space between the two markers 234 and (2) rotating the two markers away from each other 232. The fixation guide 220 is preferably made of two guide arms 226, 228, two mounting tabs 223, 225, two base arms 222, 224, and a base shaft 230. By manipulating the two guide arms 222, 224 according to the surgical plan, the osteotomy wedge may be opened precisely according to the computer-calculated optimum position based on the updated location of the multifunctional markers 110.

The two base arms 226, 228 are preferably connected to each other by a base shaft 230 that runs at least partially into and through the middle of the base arms 226, 228. The base shaft 230 allows the base arms 226, 228 to move translationally 230 (towards and away from each other down the long axis of the base shaft 230) as well as rotationally 232 (around the long axis of the base shaft 230). At the opposite ends of the base arms 226, 228 from the base shaft 230, there are preferably two mounting tabs 223, 225 and two guide arms 222, 224. The mounting tabs 223, 225 provide a surface for securing the adjustable fixation guide 220 to the multifunctional markers 110. For example, the mounting tabs 223, 225 may have a post or threaded shaft extending out from the bottom of the adjustable fixation guide 220 that can be inserted into the multifunctional markers 110.

FIG. 9B shows the adjustable fixation guide 220 mounted on the multifunctional markers 110. FIG. 9C shows an exemplary surgical plan for manipulating the two guide arms 222, 224 in order to open the wedge 102 in the osteotomy. In this example, the translation is set to 5 and the rotation Φ is set to 15. These numbers can represent degrees, millimeters, are any other dimension, or may just represent position numbers labeled on the adjustable fixation guide 220. In any case, the surgical plan enables the surgeon to accurately manipulate the guide arms 222, 224 of the adjustable fixation guide 220 to open the bone wedge 102 or otherwise relocate the bone 100. The guide arms 222, 224 may be ratcheted to prevent the bone from closing if pressure is removed from the adjustable fixation guide 220.

FIG. 9B also shows a fixation plate 240 that may be used to hold the opened wedge 102 in the appropriate position while the bone 100 heals and rebuilds itself The plate 240 may be a metal rectangle with two small holes drilled therethrough near the ends of the fixation plate 240. Preferably, while the adjustable fixation guide 220 is still connected to the multifunctional markers 110, the fixation plate 240 is secured to the open wedge-side of the bone 100. To aid in the healing process and to promote future bone growth, bone material from a bone graft may be inserted into the wedge 102 to fill in the empty space.

As stated above, it should be noted at this point that the above cutting and fixation guides are presented by way of example only. In practicing the present invention, these two guides may be combined into one cutting-fixation guide, or any number of other surgical tools or guides may be used. Likewise, the various surgical tools and/or calibration guides could be attached directly to the bone, without the use of the multifunctional markers. In this embodiment, a fluoroscopic image of the attached tool could be captured during surgery to update the surgical plan. A number of different variations on these same themes, including methods without a pre-surgical plan, could be employed within the scope of the present invention.

If the osteotomy procedure of this example includes more than one cut, the other parts of the bone may be opened at this time. As with the first procedure, the markers are placed; a fluoroscopic image is taken; a final surgical plan is developed; and the bone is cut, opened, and realigned. To save time, the marker placement and fluoroscopy for both sets of cuts may be completed at the same time. Once the final surgical plan is generated, each cut may then proceed in turn.

After the open bone wedge 102 is filled and the fixation plate 240 is secured, the adjustable fixation guide 220 is removed from the multifunctional markers 110. The markers 110 themselves are preferably removed from the patient at this point. However, in some applications of the present invention the markers may be necessary for a future surgery or adjustment and are not removed from the bone immediately after surgery. Specialized markers (not shown) may be needed if the markers are not removed. After removal, the surgical area is closed and the surgery completed. During recovery, additional X-rays or other images may be taken to determine if the osteotomy was performed successfully.

The above example described an embodiment of the present invention wherein the modeling computer, planning computer, and all necessary surgical equipment exist in the same location where the surgery is performed. A computer network, such as the Internet, may also be used to connect the operating room equipment to the planning and other computer systems. In this way, one central planning computer location can serve a plurality of different operating rooms or different hospitals. Alternatively, one central modeling computer may contain a database of template bone models that are used by a variety of different planning computers in a variety of different locations.

The entire CAOS process may occur as part of a distributed computer network. For example, the initial X-rays of the patient may be taken at a local hospital and then sent electronically to a modeling computer in a central location. The operator of the modeling computer may search a local or remote database of template bone models to determine which model most closely resembles the patient's bone. Thereafter, the "morphing" of the model may take place on this same modeling computer, in this same location, or on a separate morphing computer at a different location.

Once the "morphed" patient bone model is generated, the model is preferably sent to a planning computer which aids in the determination of the pre-surgical plan. This planning computer may be located back at the original local hospital, or it may exist in some other location. The planning computer may be operated by a local operator, or the planning computer may be run by a remote expert. For example, the operators at the central location may send a patient's medical history, X-rays, 3D template bone model, and other information to a remotely located orthopedic surgeon or other expert. This expert may use that information and his or her skill to generate the plan on a local planning computer, or the expert may send plan suggestions back to a planning computer at the central location. The particular expert chosen to assist in developing the plan may be based on that expert's area of expertise.

After the generated (or amended) pre-surgical plan has been accepted by the surgeon, the operation is performed. During the osteotomy surgery, fluoroscopic images of the marker positions are taken and then sent electronically to the planning computer (either in the same hospital or a remote location). The surgical plan can be updated, and the results of the updated surgical plan can be sent to the local hospital where the osteotomy is performed.

Because of the segmented approach to the present orthopedic surgery method, the possibilities of patient and computer locations are virtually endless. These methods provide for "remote expertise" wherein CAOS experts can oversee and run the planning computer from a central location and a plurality of surgeons from different hospitals can electronically communicate with the CAOS experts. This method may include vastly reduced costs compared to present methods, and many hospitals and offices that can not afford IR tracking equipment will now be able to perform osteotomy procedures.

The above examples focused on an open wedge osteotomy as an example of an orthopedic surgery performed using the present invention. However, this invention can be used for many different types of orthopedic surgery, as well as many other types of surgical and non-surgical applications where intra-operative feedback may be helpful. For example, the present invention could also be used for closing wedge, distraction, dome, derotational, step-cut, and other types of orthopedic surgery. With these surgeries, the basic framework of the invention remains constant, but the exact plan and surgical tools used to implement the invention may be altered.

The present invention may also be used for a total joint replacement, such as a hip or knee replacement. For example, if the hinge surface of a patient's knee is worn out, the surgeon may cut the lower portion of the femur and the upper portion of the tibia and insert a new knee joint into the patient's leg. To achieve surgical success, the surgeon needs to align the new knee joint with the existing bone structure of the patient. Traditionally, a series of jigs and/or alignment rods have been used. Using the multifunctional markers of the present invention, the surgeon may be able to more accurately align the new joint using a less invasive procedure than conventional methods.

The present invention may be used in cases of multiple trauma with long bone fractures. To realign the bone and minimize blood loss, the trauma surgeon uses an external fixator to quickly stabilize the patient. Thereafter, the surgeon may take a fluoroscopic or other image of the fractures and apply the present system to obtain an exact realignment of the fractured bone.

The present invention may also be used for oncology-related applications, such as removing a bone tumor from a patient. Generally, a surgeon performing a bone tumor removal seeks to remove only the tumorous portions of the bone while leaving the healthy tissue in tact. Because visual clues are not always available to the surgeon, the present invention may be used to develop a surgical plan and place markers around the tumor sight. An updated image of the marker position may be used to easily determine which parts of the bone are tumorous and need to be removed. Also, after the surgery, the markers may be used to make sure that the complete tumor was removed. Use of the present invention is less expensive and time consuming than the conventional MRI/CAT-based methods.

The present invention may also be used to ease the performance of complicated surgeries. For example, spine surgery may be difficult because it involves a 3D surgery around the spine in an area of the body where there may be a small margin for error. The multifunctional markers and fixation devices may allow the surgery to be performed more precisely, and in a reduced amount of time.

The present invention may also be used to perform intramedullary procedures on a patient's bone. In such a procedure, a rod is inserted inside the hollow of a bone down its long axis. Near at least one end of the rod, there is an elliptical hole that accepts a screw to prevent the rod from rotating or twisting within the bone. In conventional methods, it is often difficult to accurately locate the elliptical hole for the set screw. Using the multifunctional markers and fixation devices of the present invention, localization would be more easily accomplished.

For example, the updated marker position may be used to provide settings as part of a surgical plan for a device that allows the insertion of the set screw. Rather than searching within the patient to find the elliptical hole, the surgeon can set the fixation device and insert the screw with confidence that the hole will be beneath the device.

The present invention may be used in a similar manner to the above methods for performing localization and surgical procedures on bone lesions, any soft tissues, and/or maxilofacial surgery. In general, the embodiments and features of the present invention may be specifically suited to aiding in the performance of many or all bone and soft tissue procedures.

The above specification describes several different embodiments and features of a device and method for performing orthopedic surgery. Various parts, selections, and/or alternatives from the various embodiments may preferably be interchanged with other parts of different embodiments. Although the invention has been described above in terms of particular embodiments, one of ordinary skill in the art, in light of the teachings herein, can generate additional embodiments and modifications without departing from the spirit of, or exceeding the scope of, the claimed invention. Accordingly, it is to be understood that the drawings and the descriptions herein are proffered only by way of example only to facilitate comprehension of the invention and should not be construed to limit the scope thereof.

What is claimed is:

1. A method of generating an updated surgical plan, the method comprising:

generating a three dimensional (3D) model of a bone;

based on the 3D model, generating a surgical plan including:
    one or more locations on the bone upon which to dispose one or more markers for receiving one or more guides for guiding one or more surgical tools, and
    one or more settings of the one or more guides;

based on the surgical plan, disposing the one or more markers on the bone; and, based on data associated with the placement of the one or more markers disposed on the bone, generating an updated surgical plan including updated settings for the one or more guides.

2. The method of claim 1, wherein the one or more guides comprise an adjustable cutting guide.

3. The method of claim 2, wherein the adjustable cutting guide includes settings for one or more of an angle in a plane parallel to the bone and an angle in a plane perpendicular to the bone.

4. The method of claim 1, wherein the one or more guides comprise an adjustable fixation guide.

5. The method of claim 4, wherein the adjustable fixation guide includes settings for one or more of an angle in a plane parallel to the bone and an angle in a plane perpendicular to the bone.

6. The method of claim 1, wherein the one or more guides comprise an adjustable combined cutting-fixation guide.

7. The method of claim 1, wherein the data comprise one or more images of the bone.

8. The method of claim 7, wherein the one or more images include one or more X-ray images.

9. The method of claim 7, wherein the one or more images include one or more fluoroscopic images.

10. The method of claim 9, wherein the one or more fluoroscopic images include one or more calibration grid points used to unwarp the fluoroscopic images.

11. The method of claim 1, wherein the one or more surgical tools are attached to an area of the bone designated for a surgical procedure.

12. The method of claim 1, wherein the one or more markers are radio-opaque.

13. The method of claim 1, wherein the one or more markers are capable of anchoring the one or more surgical tools to an area of the bone designated for a surgical procedure.

14. The method of claim 1, wherein the one or more locations of the one or more markers includes a range of acceptable marker locations.

15. The method of claim 1, wherein the one or more locations include one or more locations for an osteotomy.

16. The method of claim 1, wherein the one or more surgical tools include one or more calibration grids.

17. The method of claim 1, wherein generating the surgical plan comprises:
receiving at a server images of the bone from a client;
generating the surgical plan at the server; and,
providing the surgical plan from the server to the client; and,
wherein generating the updated surgical plan includes:
receiving at the server the data associated with the placement of the one or more markers from the client;
generating the updated surgical plan at the server, and
providing the updated surgical plan from the server to the client.

18. The method of claim 17, wherein the one or more images include one or more X-ray images of the bone.

19. The method of claim 17, wherein the one or more images are orthogonal to each other.

20. The method of claim 17, wherein the data associated with the placement of the one or more markers include one or more fluoroscopic images of the bone.

21. The method of claim 1, wherein generating a surgical plan includes performing a numerical analysis on the 3D model of the bone.

22. The method of claim 21, wherein the numerical analysis is an iterative analysis.

23. The method of claim 21, wherein performing a numerical analysis comprises:
virtually cutting the 3D model of the bone at one or more first locations along an axis of the bone;
repositioning the 3D model along a selected mechanical axis; and
determining a first deviation between the positions of the 3D model before and after repositioning the 3D model.

24. The method of claim 23, wherein performing a numerical analysis further comprises:
for each of the one or more first locations, virtually cutting the 3D model at one or more second locations along the axis of the bone;
performing a second repositioning of the 3D model along the selected mechanical axis;
determining a second deviation between the positions of the 3D model before and after performing the second repositioning of the 3D model ; and
identifying the first and second locations corresponding to a minimum value of the combined first and second deviations.

25. The method of claim 1, wherein generating a 3D model includes:
generating a 3D model based on one or more two dimensional (2D) images of the bone and one or more 3D bone templates.

26. The method of claim 1, further comprising:
generating one or more 2D images of the bone with the one or more markers disposed on the bone, and
wherein generating an updated surgical plan includes:
generating the updated surgical plan based on the 2D images.

27. The method of claim 26, further comprising:
calibrating the 2D images, and
wherein generating an updated surgical plan includes:
generating an updated surgical plan based on the calibrated 2D images.

28. The method of claim 26, wherein the 2D images include one or more of X-ray images and fluoroscopic images.

29. A method for generating an updated surgical plan, the method comprising:
generating a three dimensional (3D) model of a bone,
based on the 3D model, generating a surgical plan including:
one or more locations on the bone upon which to dispose one or more guides for guiding one or more surgical tools, and
one or more settings of the one or more guides,
based on the surgical plan, disposing the one or more guides on the bone, and
based on data associated with the placement of the one or more guides disposed on the bone, generating an updated surgical plan including updated settings for the guides.

30. The method of claim 29, wherein generating a 3D model includes:
generating a 3D model based on one or more two dimensional (2D) images of the bone and one or more 3D bone templates.

31. The method of claim 30, wherein the 2D images include one or more of X-ray images and fluoroscopic images.

32. The method of claim 30, wherein the 2D images are orthogonal to each other.

33. The method of claim 29, wherein the one or more guides include one or more of an adjustable cutting guide, an adjustable fixation guide, and an adjustable cutting-fixation guide.

34. The method of claim 29, wherein the one or more guides include settings for one or more of an angle in a plane parallel to the bone and an angle in a plane perpendicular to the bone.

35. The method of claim 29, wherein the data associated with the placement of the one or more guides on the bone include one or more of X-ray images and fluoroscopic images.

36. The method of claim 35, wherein the images are orthogonal to each other.

37. A method for generating an updated surgical plan, the method comprising:
generating a three dimensional (3D) model of a bone,
based on the 3D model, generating a surgical plan including:
one or more locations on the bone upon which to dispose one or more surgical tools, and one or more instructions for using the one or more surgical tools, based on the surgical plan, disposing the one or more surgical tools on the bone, and based on data associated with the placement of the one or more surgical tools disposed on the bone, generating an updated surgical plan including updated instructions for the one or more surgical tools.

38. The method of claim 37, wherein generating a 3D model includes:

generating a 3D model based on one or more two dimensional (2D) images of the bone and one or more 3D bone templates.

39. The method of claim 38, wherein the 2D images include one or more of X-ray images and fluoroscopic images.

40. The method of claim 38, wherein the 2D images are orthogonal to each other.

41. The method of claim 37, wherein the one or more guides include one or more of an adjustable cutting guide, an adjustable fixation guide, and an adjustable cutting-fixation guide.

42. The method of claim 37, wherein the one or more guides include settings for one or more of an angle in a plane parallel to the bone and an angle in a plane perpendicular to the bone.

43. The method of claim 37, wherein the data associated with the placement of the one or more surgical tools on the bone include one or more of X-ray images and fluoroscopic images.

44. The method of claim 43, wherein the images are orthogonal to each other.

* * * * *